(12) United States Patent
Powers et al.

(10) Patent No.: US 7,883,502 B2
(45) Date of Patent: Feb. 8, 2011

(54) CONNECTOR SYSTEM FOR A PROXIMALLY TRIMMABLE CATHETER

(75) Inventors: Kelly B. Powers, North Salt Lake, UT (US); Catherine C. Breiter, Holladay, UT (US); Jordan P. Diamond, Salt Lake City, UT (US); Jason R. Stats, Layton, UT (US); Daniel J. Triplett, Providence, UT (US)

(73) Assignee: C. R. Bard, Inc., Murray Hill, NJ (US)

( * ) Notice: Subject to any disclaimer, the term of this patent is extended or adjusted under 35 U.S.C. 154(b) by 0 days.

(21) Appl. No.: 12/563,776

(22) Filed: Sep. 21, 2009

(65) Prior Publication Data

US 2010/0010445 A1    Jan. 14, 2010

Related U.S. Application Data

(62) Division of application No. 10/803,513, filed on Mar. 18, 2004, now Pat. No. 7,594,911.

(51) Int. Cl.
*A61M 25/00* (2006.01)
(52) U.S. Cl. .................................... 604/523
(58) Field of Classification Search ................ 604/905, 604/533, 523, 264, 534, 535
See application file for complete search history.

(56) References Cited

U.S. PATENT DOCUMENTS

| | | | |
|---|---|---|---|
| 2,471,623 A | 5/1949 | Hubbell | |
| 2,709,542 A | 5/1955 | Eller | |
| 3,176,690 A | 4/1965 | H'Doubler | |
| D217,795 S | 6/1970 | Spaven | |
| 3,527,226 A | 9/1970 | Hakim | |
| 3,565,078 A | 2/1971 | Vailliancourt et al. | |
| 3,572,340 A | 3/1971 | Lloyd et al. | |
| 3,650,507 A | 3/1972 | Nyberg et al. | |
| 3,672,372 A | 6/1972 | Heimlich | |
| 3,805,794 A | 4/1974 | Schlesinger | |
| 3,921,631 A | 11/1975 | Thompson | |
| 4,000,739 A | 1/1977 | Stevens | |
| 4,029,095 A | 6/1977 | Pena et al. | |
| 4,068,659 A | 1/1978 | Moorehead | |

(Continued)

FOREIGN PATENT DOCUMENTS

EP    0183396 A1    6/1986

(Continued)

OTHER PUBLICATIONS

Jun. 7, 2005 International Search Report in international application No. PCT/US2005/009150.

(Continued)

*Primary Examiner*—Manuel A Mendez
(74) *Attorney, Agent, or Firm*—Rutan & Tucker, LLP

(57) ABSTRACT

A catheter connector system for a subcutaneously placed catheter. The catheter connector system permits proximal trimming of the placed catheter, which is a procedure that provides numerous advantages over traditional methods of trimming catheter distal ends prior to implantation. The catheter connector system can be configured for a single lumen catheter or a multiple lumen catheter. The catheter connector system facilitates precise positioning of both distal and proximal ends of a catheter, providing enhanced functionability and patient comfort.

20 Claims, 16 Drawing Sheets

U.S. PATENT DOCUMENTS

| | | | |
|---|---|---|---|
| 4,112,949 A | 9/1978 | Rosenthal et al. | |
| 4,123,091 A | 10/1978 | Cosentino et al. | |
| 4,134,402 A | 1/1979 | Mahurkar | |
| 4,198,973 A | 4/1980 | Millet | |
| 4,233,974 A | 11/1980 | Desecki et al. | |
| 4,235,232 A | 11/1980 | Spaven et al. | |
| 4,256,106 A | 3/1981 | Shoor | |
| 4,256,116 A | 3/1981 | Meretsky et al. | |
| 4,267,835 A | 5/1981 | Barger et al. | |
| 4,296,747 A | 10/1981 | Ogle | |
| 4,306,562 A | 12/1981 | Osborne | |
| 4,340,052 A | 7/1982 | Dennehey et al. | |
| 4,387,879 A | 6/1983 | Tauschinski et al. | |
| 4,391,029 A | 7/1983 | Czuba et al. | |
| 4,411,654 A | 10/1983 | Boarini et al. | |
| 4,412,832 A | 11/1983 | Kling et al. | |
| 4,424,833 A | 1/1984 | Spector et al. | |
| D272,651 S | 2/1984 | Mahurkar | |
| 4,430,081 A | 2/1984 | Timmermans | |
| 4,431,426 A | 2/1984 | Groshong et al. | |
| 4,432,759 A | 2/1984 | Gross et al. | |
| 4,436,519 A | 3/1984 | O'Neill | |
| 4,439,179 A | 3/1984 | Lueders et al. | |
| 4,445,893 A | 5/1984 | Bodicky | |
| 4,449,973 A | 5/1984 | Luther | |
| 4,468,224 A | 8/1984 | Enzmann et al. | |
| 4,473,067 A | 9/1984 | Schiff | |
| 4,490,003 A | 12/1984 | Robinson | |
| RE31,855 E | 3/1985 | Osborne | |
| 4,512,766 A | 4/1985 | Vailancourt | |
| 4,539,003 A | 9/1985 | Tucker | |
| 4,543,087 A | 9/1985 | Sommercorn et al. | |
| 4,553,959 A | 11/1985 | Hickey et al. | |
| 4,557,261 A | 12/1985 | Rugheimer et al. | |
| 4,568,329 A | 2/1986 | Mahurkar | |
| 4,571,241 A | 2/1986 | Christopher | |
| 4,573,974 A | 3/1986 | Ruschke | |
| 4,581,012 A | 4/1986 | Brown et al. | |
| 4,581,025 A | 4/1986 | Timmermans | |
| 4,583,968 A | 4/1986 | Mahurkar | |
| 4,591,355 A | 5/1986 | Hilse | |
| 4,592,749 A | 6/1986 | Ebling et al. | |
| 4,596,559 A | 6/1986 | Fleischhacker | |
| 4,596,571 A | 6/1986 | Bellotti et al. | |
| 4,610,665 A | 9/1986 | Matsumoto et al. | |
| 4,619,643 A | 10/1986 | Bai | |
| 4,623,327 A | 11/1986 | Mahurkar | |
| 4,626,245 A | 12/1986 | Weinstein | |
| 4,643,711 A | 2/1987 | Bates | |
| 4,650,472 A | 3/1987 | Bates | |
| 4,673,393 A | 6/1987 | Suzuki et al. | |
| 4,675,004 A | 6/1987 | Hadford et al. | |
| 4,675,020 A | 6/1987 | McPhee | |
| 4,681,122 A | 7/1987 | Winters et al. | |
| 4,682,978 A | 7/1987 | Martin et al. | |
| 4,692,141 A | 9/1987 | Mahurkar | |
| 4,701,159 A | 10/1987 | Brown et al. | |
| 4,722,725 A | 2/1988 | Sawyer et al. | |
| 4,723,550 A | 2/1988 | Bales et al. | |
| 4,723,948 A | 2/1988 | Clark et al. | |
| 4,726,374 A | 2/1988 | Bales et al. | |
| 4,738,658 A * | 4/1988 | Magro et al. | 604/537 |
| 4,743,265 A | 5/1988 | Whitehouse et al. | |
| 4,747,833 A | 5/1988 | Kousai et al. | |
| 4,753,765 A | 6/1988 | Pande | |
| 4,770,652 A | 9/1988 | Mahurkar | |
| 4,772,266 A | 9/1988 | Groshong | |
| 4,772,268 A | 9/1988 | Bates | |
| 4,776,841 A | 10/1988 | Catalano | |
| 4,784,644 A | 11/1988 | Sawyer et al. | |
| 4,795,426 A | 1/1989 | Jones | |
| 4,798,594 A | 1/1989 | Hillstead | |
| 4,808,155 A | 2/1989 | Mahurkar | |
| 4,842,582 A | 6/1989 | Mahurkar | |
| 4,842,592 A | 6/1989 | Caggiani et al. | |
| 4,850,955 A | 7/1989 | Newkirk | |
| 4,865,593 A | 9/1989 | Ogawa et al. | |
| 4,874,377 A | 10/1989 | Newgard et al. | |
| 4,895,561 A * | 1/1990 | Mahurkar | 604/43 |
| 4,909,798 A | 3/1990 | Fleischhacker et al. | |
| RE33,219 E | 5/1990 | Daniell et al. | |
| 4,921,479 A | 5/1990 | Grayzel | |
| 4,929,235 A | 5/1990 | Merry et al. | |
| 4,929,236 A | 5/1990 | Sampson | |
| 4,932,633 A | 6/1990 | Johnson et al. | |
| 4,932,938 A | 6/1990 | Goldberg et al. | |
| 4,935,010 A | 6/1990 | Cox et al. | |
| 4,936,826 A | 6/1990 | Amarasinghe | |
| 4,946,133 A | 8/1990 | Johnson et al. | |
| 4,946,449 A | 8/1990 | Davis, Jr. | |
| 4,952,359 A | 8/1990 | Wells | |
| 4,960,412 A | 10/1990 | Fink | |
| 4,966,588 A | 10/1990 | Rayman et al. | |
| 4,983,168 A | 1/1991 | Moorehead | |
| 4,997,424 A | 3/1991 | Little | |
| 5,007,901 A | 4/1991 | Shields | |
| 5,035,686 A | 7/1991 | Crittenden et al. | |
| 5,041,095 A | 8/1991 | Littrell | |
| 5,053,003 A | 10/1991 | Dadson et al. | |
| 5,053,004 A | 10/1991 | Markel et al. | |
| 5,053,013 A | 10/1991 | Ensminger et al. | |
| 5,053,014 A | 10/1991 | Van Heugten | |
| 5,053,023 A | 10/1991 | Martin et al. | |
| 5,057,073 A | 10/1991 | Martin et al. | |
| 5,059,170 A | 10/1991 | Cameron | |
| 5,064,414 A | 11/1991 | Revane | |
| 5,066,285 A * | 11/1991 | Hillstead | 604/164.01 |
| 5,071,411 A | 12/1991 | Hillstead | |
| 5,078,688 A | 1/1992 | Lobodzinski et al. | |
| 5,085,645 A | 2/1992 | Purdy et al. | |
| 5,092,857 A | 3/1992 | Fleischhacker | |
| 5,098,392 A | 3/1992 | Fleischhacker et al. | |
| 5,098,393 A | 3/1992 | Amplatz et al. | |
| 5,106,368 A | 4/1992 | Uldall et al. | |
| 5,108,380 A | 4/1992 | Herlitze et al. | |
| 5,112,301 A | 5/1992 | Fenton, Jr. et al. | |
| 5,112,323 A | 5/1992 | Winkler et al. | |
| 5,114,408 A | 5/1992 | Fleischhaker et al. | |
| 5,117,836 A | 6/1992 | Millar | |
| 5,125,904 A | 6/1992 | Lee | |
| 5,135,599 A | 8/1992 | Martin et al. | |
| 5,137,524 A | 8/1992 | Lynn et al. | |
| 5,141,497 A | 8/1992 | Erskine | |
| 5,149,327 A | 9/1992 | Oshiyama et al. | |
| 5,154,701 A | 10/1992 | Cheer et al. | |
| 5,156,592 A | 10/1992 | Martin et al. | |
| 5,156,596 A | 10/1992 | Balbierz et al. | |
| 5,158,545 A | 10/1992 | Trudell et al. | |
| 5,158,553 A | 10/1992 | Berry et al. | |
| 5,160,323 A | 11/1992 | Andrew et al. | |
| 5,163,903 A | 11/1992 | Crittenden et al. | |
| 5,167,634 A | 12/1992 | Corrigan, Jr. et al. | |
| 5,167,637 A | 12/1992 | Okada et al. | |
| 5,169,393 A | 12/1992 | Moorehead et al. | |
| 5,171,222 A | 12/1992 | Euteneuer et al. | |
| 5,180,372 A | 1/1993 | Vegoe et al. | |
| 5,186,431 A | 2/1993 | Tamari | |
| 5,188,593 A | 2/1993 | Martin et al. | |
| 5,190,520 A | 3/1993 | Fenton, Jr. et al. | |
| 5,190,528 A | 3/1993 | Fonger et al. | |
| 5,190,529 A | 3/1993 | McCrory et al. | |
| 5,191,898 A | 3/1993 | Millar | |
| 5,195,962 A | 3/1993 | Martin et al. | |
| 5,197,951 A | 3/1993 | Mahurkar | |

| | | | | | |
|---|---|---|---|---|---|
| 5,197,976 A | 3/1993 | Herweck et al. | 5,472,417 A | 12/1995 | Martin et al. |
| 5,201,722 A | 4/1993 | Moorehead et al. | 5,472,418 A | 12/1995 | Palestrant |
| 5,205,834 A | 4/1993 | Moorehead et al. | 5,472,432 A | 12/1995 | Martin et al. |
| 5,207,650 A | 5/1993 | Martin et al. | 5,472,435 A | 12/1995 | Sutton |
| 5,209,723 A | 5/1993 | Twardowski et al. | 5,474,099 A | 12/1995 | Boehmer et al. |
| 5,211,633 A | 5/1993 | Stouder, Jr. | 5,474,540 A | 12/1995 | Miller et al. |
| 5,215,538 A | 6/1993 | Larkin | 5,480,380 A | 1/1996 | Martin et al. |
| 5,221,255 A | 6/1993 | Mahurkar et al. | 5,484,401 A | 1/1996 | Rodriguez et al. |
| 5,221,256 A | 6/1993 | Mahurkar | 5,486,159 A | 1/1996 | Mahurkar |
| 5,221,263 A | 6/1993 | Sinko et al. | 5,488,960 A | 2/1996 | Toner |
| 5,234,410 A | 8/1993 | Graham et al. | 5,496,299 A | 3/1996 | Felix et al. |
| 5,242,413 A | 9/1993 | Heiliger | 5,496,346 A | 3/1996 | Horzewski et al. |
| 5,242,430 A | 9/1993 | Arenas et al. | 5,501,676 A | 3/1996 | Niedospial et al. |
| 5,250,033 A | 10/1993 | Evans et al. | 5,507,733 A | 4/1996 | Larkin et al. |
| 5,251,873 A | 10/1993 | Atkinson et al. | 5,509,897 A | 4/1996 | Twardowski et al. |
| 5,255,691 A | 10/1993 | Otten | 5,514,117 A | 5/1996 | Lynn |
| 5,273,540 A | 12/1993 | Luther et al. | 5,520,655 A | 5/1996 | Davila et al. |
| 5,273,546 A | 12/1993 | McLaughlin et al. | 5,520,665 A | 5/1996 | Fleetwood et al. |
| 5,275,583 A | 1/1994 | Crainich | 5,522,806 A | 6/1996 | Schonbachler et al. |
| 5,279,597 A | 1/1994 | Dassa et al. | 5,536,255 A | 7/1996 | Moss |
| 5,290,294 A | 3/1994 | Cox et al. | 5,538,505 A | 7/1996 | Weinstein et al. |
| 5,304,142 A | 4/1994 | Liebl et al. | 5,542,931 A | 8/1996 | Gravener et al. |
| 5,304,156 A | 4/1994 | Sylvanowicz et al. | 5,556,387 A | 9/1996 | Mollenauer et al. |
| 5,312,337 A * | 5/1994 | Flaherty et al. ............. 285/278 | 5,569,182 A | 10/1996 | Twardowski et al. |
| 5,312,355 A | 5/1994 | Lee | 5,599,305 A | 2/1997 | Hermann et al. |
| 5,312,357 A | 5/1994 | Buijs et al. | 5,613,953 A | 3/1997 | Pohndorf |
| 5,320,602 A | 6/1994 | Karpiel | 5,613,956 A | 3/1997 | Patterson et al. |
| 5,324,271 A | 6/1994 | Abiuso et al. | 5,624,413 A | 4/1997 | Markel et al. |
| 5,324,274 A | 6/1994 | Martin et al. | 5,632,729 A | 5/1997 | Cai et al. |
| 5,330,437 A | 7/1994 | Durman | 5,636,875 A | 6/1997 | Wasser et al. |
| 5,334,157 A | 8/1994 | Klein et al. | 5,637,102 A | 6/1997 | Tolkoff et al. |
| 5,334,187 A | 8/1994 | Fischell et al. | 5,647,857 A | 7/1997 | Anderson et al. |
| 5,336,192 A | 8/1994 | Palestrant | 5,651,776 A | 7/1997 | Appling et al. |
| 5,338,313 A | 8/1994 | Mollenauer et al. | 5,653,698 A | 8/1997 | Niedospial et al. |
| 5,342,386 A | 8/1994 | Trotta | 5,672,158 A | 9/1997 | Okada et al. |
| 5,348,537 A | 9/1994 | Wiesner et al. | 5,685,856 A | 11/1997 | Lehrer |
| 5,350,358 A | 9/1994 | Martin et al. | 5,685,867 A | 11/1997 | Twardowski et al. |
| 5,350,362 A | 9/1994 | Stouder, Jr. | 5,702,370 A | 12/1997 | Sylvanowicz et al. |
| 5,350,363 A | 9/1994 | Goode et al. | 5,702,374 A | 12/1997 | Johnson |
| 5,360,397 A | 11/1994 | Pinchuk | 5,704,915 A | 1/1998 | Melsky et al. |
| 5,360,403 A | 11/1994 | Mische | 5,713,867 A | 2/1998 | Morris |
| 5,364,393 A | 11/1994 | Auth et al. | 5,718,678 A | 2/1998 | Fleming, III |
| 5,368,574 A | 11/1994 | Antonacci et al. | 5,718,692 A | 2/1998 | Schon et al. |
| 5,374,245 A | 12/1994 | Mahurkar | 5,725,506 A | 3/1998 | Freeman et al. |
| 5,378,230 A | 1/1995 | Mahurkar | 5,735,819 A | 4/1998 | Elliott |
| 5,380,276 A | 1/1995 | Miller et al. | 5,741,233 A | 4/1998 | Riddle et al. |
| 5,382,241 A | 1/1995 | Choudhury et al. | 5,752,937 A | 5/1998 | Otten et al. |
| 5,389,090 A | 2/1995 | Fischell et al. | 5,755,693 A | 5/1998 | Walker et al. |
| 5,391,152 A | 2/1995 | Patterson | 5,755,702 A | 5/1998 | Hillstead et al. |
| 5,395,352 A | 3/1995 | Penny | 5,766,203 A | 6/1998 | Imran et al. |
| 5,397,311 A | 3/1995 | Walker et al. | 5,772,628 A | 6/1998 | Bacich et al. |
| 5,399,172 A | 3/1995 | Martin et al. | 5,772,643 A | 6/1998 | Howell et al. |
| 5,401,245 A | 3/1995 | Haining | 5,772,678 A | 6/1998 | Thomason et al. |
| 5,405,320 A | 4/1995 | Twardowski et al. | 5,776,111 A | 7/1998 | Tesio et al. |
| 5,405,323 A | 4/1995 | Rogers et al. | 5,782,505 A | 7/1998 | Brooks et al. |
| 5,405,341 A | 4/1995 | Martin et al. | 5,782,807 A | 7/1998 | Falvai et al. |
| 5,407,434 A | 4/1995 | Gross | 5,782,817 A | 7/1998 | Franzel et al. |
| 5,409,463 A | 4/1995 | Thomas et al. | 5,785,694 A | 7/1998 | Cohen et al. |
| 5,409,464 A | 4/1995 | Villalobos | 5,797,869 A | 8/1998 | Martin et al. |
| 5,409,469 A | 4/1995 | Schaerf | 5,800,414 A | 9/1998 | Cazal et al. |
| 5,409,644 A | 4/1995 | Martin et al. | 5,807,311 A | 9/1998 | Palestrant |
| 5,413,561 A | 5/1995 | Fischell et al. | 5,810,789 A | 9/1998 | Powers et al. |
| 5,415,320 A | 5/1995 | North et al. | 5,843,031 A | 12/1998 | Hermann et al. |
| 5,417,668 A | 5/1995 | Setzer et al. | 5,843,046 A | 12/1998 | Motisi et al. |
| 5,419,340 A | 5/1995 | Stevens | 5,853,393 A | 12/1998 | Bogert |
| 5,423,762 A | 6/1995 | Hillstead | 5,858,007 A | 1/1999 | Fagan et al. |
| 5,429,616 A | 7/1995 | Schaffer | 5,865,721 A | 2/1999 | Andrews et al. |
| 5,437,645 A | 8/1995 | Urban et al. | 5,879,333 A | 3/1999 | Smith et al. |
| 5,441,504 A | 8/1995 | Pohndorf et al. | 5,885,217 A | 3/1999 | Gisselberg et al. |
| 5,445,613 A | 8/1995 | Orth | 5,895,376 A | 4/1999 | Schwartz et al. |
| 5,453,095 A | 9/1995 | Davila et al. | 5,897,533 A | 4/1999 | Glickman |
| 5,454,409 A | 10/1995 | McAffer et al. | 5,911,710 A | 6/1999 | Barry et al. |
| 5,460,616 A | 10/1995 | Weinstein et al. | 5,916,194 A | 6/1999 | Jacobsen et al. |

| | | | | | | |
|---|---|---|---|---|---|---|
| 5,919,160 A | 7/1999 | Sanfilippo, II | | 6,508,807 B1 | 1/2003 | Peters |
| 5,921,968 A | 7/1999 | Lampropoulos et al. | | 6,520,939 B1 | 2/2003 | Lafontaine |
| 5,935,112 A | 8/1999 | Stevens et al. | | 6,544,247 B1 | 4/2003 | Gardeski et al. |
| 5,944,695 A | 8/1999 | Johnson et al. | | 6,551,283 B1 | 4/2003 | Guo et al. |
| 5,944,732 A | 8/1999 | Raulerson et al. | | 6,562,023 B1 | 5/2003 | Marrs et al. |
| 5,947,953 A | 9/1999 | Ash et al. | | 6,575,960 B2 | 6/2003 | Becker et al. |
| 5,951,518 A | 9/1999 | Licata et al. | | 6,589,262 B1 | 7/2003 | Honebrink et al. |
| 5,957,912 A | 9/1999 | Heitzmann | | 6,592,544 B1 | 7/2003 | Mooney et al. |
| 5,961,485 A | 10/1999 | Martin et al. | | 6,592,558 B2 | 7/2003 | Quah et al. |
| 5,961,486 A | 10/1999 | Twardowski et al. | | 6,592,565 B2 | 7/2003 | Twardowski |
| 5,967,490 A | 10/1999 | Pike | | 6,623,460 B1 | 9/2003 | Heck |
| 5,971,958 A | 10/1999 | Zhang | | 6,626,418 B2 | 9/2003 | Kiehne et al. |
| 5,976,103 A | 11/1999 | Martin et al. | | 6,629,350 B2 | 10/2003 | Motsenbocker |
| 5,989,213 A | 11/1999 | Maginot | | 6,632,200 B2 | 10/2003 | Guo et al. |
| 5,997,486 A | 12/1999 | Burek et al. | | 6,638,242 B2 | 10/2003 | Wilson et al. |
| 6,024,729 A | 2/2000 | Dehdashtian et al. | | 6,641,574 B2 | 11/2003 | Badia Segura et al. |
| 6,027,480 A | 2/2000 | Davis et al. | | 6,645,178 B1 | 11/2003 | Junker et al. |
| 6,033,375 A | 3/2000 | Brumbach | | 6,663,595 B2 | 12/2003 | Spohn et al. |
| 6,033,388 A | 3/2000 | Nordstrom et al. | | 6,669,681 B2 | 12/2003 | Jepson et al. |
| 6,036,171 A | 3/2000 | Weinheimer et al. | | 6,682,498 B2 | 1/2004 | Ross |
| 6,053,904 A | 4/2000 | Scribner et al. | | 6,682,519 B1 | 1/2004 | Schon |
| 6,068,011 A | 5/2000 | Paradis | | 6,689,109 B2 | 2/2004 | Lynn |
| 6,074,374 A | 6/2000 | Fulton | | 6,692,464 B2 | 2/2004 | Graf |
| 6,074,377 A | 6/2000 | Sanfilippo, II | | 6,695,832 B2 | 2/2004 | Schon et al. |
| 6,074,379 A | 6/2000 | Prichard | | 6,712,796 B2 | 3/2004 | Fentis et al. |
| 6,083,207 A | 7/2000 | Heck | | 6,719,749 B1 | 4/2004 | Schweikert et al. |
| 6,086,555 A | 7/2000 | Eliasen et al. | | 6,722,705 B2 | 4/2004 | Korkor |
| 6,086,570 A | 7/2000 | Aboul-Hosn et al. | | 6,827,710 B1 | 12/2004 | Mooney et al. |
| 6,088,889 A | 7/2000 | Luther et al. | | 6,843,513 B2 | 1/2005 | Guala |
| 6,090,083 A | 7/2000 | Sell et al. | | 6,872,198 B1 | 3/2005 | Wilson et al. |
| 6,093,154 A | 7/2000 | Burek et al. | | 6,881,211 B2 | 4/2005 | Schweikert et al. |
| 6,096,011 A | 8/2000 | Trombley, III et al. | | D505,202 S | 5/2005 | Chesnin |
| 6,099,519 A | 8/2000 | Olsen et al. | | 6,887,220 B2 | 5/2005 | Hogendijk |
| 6,106,503 A | 8/2000 | Pfeiderer et al. | | 6,893,056 B2 | 5/2005 | Guala |
| 6,106,540 A | 8/2000 | White et al. | | 6,916,051 B2 | 7/2005 | Fisher |
| 6,120,476 A | 9/2000 | Fung et al. | | 6,916,313 B2 | 7/2005 | Cunningham |
| 6,120,480 A | 9/2000 | Zhang et al. | | 6,921,396 B1 | 7/2005 | Wilson et al. |
| 6,132,407 A | 10/2000 | Genese et al. | | 6,932,795 B2 | 8/2005 | Lopez et al. |
| 6,142,981 A | 11/2000 | Heck et al. | | 6,969,381 B2 | 11/2005 | Voorhees |
| 6,155,610 A | 12/2000 | Godeau et al. | | 6,971,390 B1 | 12/2005 | Vasek et al. |
| 6,156,016 A | 12/2000 | Maginot | | 7,044,441 B2 | 5/2006 | Doyle |
| 6,159,198 A | 12/2000 | Gardeski et al. | | 7,048,724 B2 | 5/2006 | Grossman et al. |
| 6,162,196 A | 12/2000 | Hart et al. | | 7,094,218 B2 | 8/2006 | Rome et al. |
| 6,171,281 B1 | 1/2001 | Zhang | | 7,163,531 B2 | 1/2007 | Seese et al. |
| 6,179,806 B1 | 1/2001 | Sansoucy | | 7,182,746 B2 | 2/2007 | Haarala et al. |
| 6,190,349 B1 | 2/2001 | Ash et al. | | 7,258,685 B2 | 8/2007 | Kerr |
| 6,190,352 B1 | 2/2001 | Haarala et al. | | 7,300,430 B2 | 11/2007 | Wilson et al. |
| 6,190,371 B1 | 2/2001 | Maginot et al. | | 7,347,853 B2 | 3/2008 | DiFiore et al. |
| 6,206,849 B1 | 3/2001 | Martin et al. | | 7,377,915 B2 | 5/2008 | Rasmussen et al. |
| 6,210,366 B1 | 4/2001 | Sanfilippo, II | | 7,470,261 B2 | 12/2008 | Lynn |
| 6,213,988 B1 | 4/2001 | McIvor et al. | | 7,578,803 B2 | 8/2009 | Rome et al. |
| 6,221,057 B1 | 4/2001 | Schwartz et al. | | 7,594,910 B2 | 9/2009 | Butts et al. |
| 6,228,060 B1 | 5/2001 | Howell | | 7,594,911 B2 | 9/2009 | Powers et al. |
| 6,228,062 B1 | 5/2001 | Howell et al. | | 2001/0041857 A1 | 11/2001 | Sansoucy |
| 6,258,058 B1 | 7/2001 | Sanfilippo, II | | 2001/0041873 A1 | 11/2001 | Dopper et al. |
| 6,273,871 B1 | 8/2001 | Davis et al. | | 2002/0010437 A1 | 1/2002 | Lopez et al. |
| 6,276,661 B1 | 8/2001 | Laird | | 2002/0077605 A1 | 6/2002 | Fentis et al. |
| 6,293,927 B1 | 9/2001 | McGuckin, Jr. | | 2002/0099326 A1 | 7/2002 | Wilson et al. |
| 6,322,541 B2 | 11/2001 | West et al. | | 2002/0099327 A1 | 7/2002 | Wilson et al. |
| 6,331,176 B1 | 12/2001 | Becker et al. | | 2002/0128604 A1 | 9/2002 | Nakajima |
| 6,332,874 B1 | 12/2001 | Eliasen et al. | | 2002/0147431 A1 | 10/2002 | Lopez et al. |
| 6,338,725 B1 | 1/2002 | Hermann et al. | | 2003/0065288 A1 | 4/2003 | Brimhall et al. |
| 6,344,033 B1 | 2/2002 | Jepson et al. | | 2003/0066218 A1 | 4/2003 | Schweikert |
| 6,352,520 B1 | 3/2002 | Miyazaki et al. | | 2003/0088213 A1 | 5/2003 | Schweikert et al. |
| 6,402,723 B1 | 6/2002 | Lampropoulos et al. | | 2003/0153898 A1 | 8/2003 | Schon et al. |
| 6,413,250 B1 | 7/2002 | Smith et al. | | 2003/0187411 A1 | 10/2003 | Constantz |
| 6,423,050 B1 | 7/2002 | Twardowski | | 2003/0199853 A1 | 10/2003 | Olsen et al. |
| 6,423,053 B1 | 7/2002 | Lee | | 2003/0201639 A1 | 10/2003 | Korkor |
| 6,454,744 B1 | 9/2002 | Spohn et al. | | 2003/0225379 A1 | 12/2003 | Schaffer et al. |
| 6,458,103 B1 | 10/2002 | Albert et al. | | 2004/0065333 A1 | 4/2004 | Wilson et al. |
| 6,494,860 B2 | 12/2002 | Rocamora et al. | | 2004/0082923 A1 | 4/2004 | Field |
| 6,497,681 B1 | 12/2002 | Brenner | | 2004/0092863 A1 | 5/2004 | Raulerson et al. |
| 6,508,790 B1 | 1/2003 | Lawrence | | 2004/0097903 A1 | 5/2004 | Raulerson |

| | | | |
|---|---|---|---|
| 2004/0122418 A1 | 6/2004 | Voorhees | |
| 2004/0158208 A1 | 8/2004 | Hiejima | |
| 2004/0167463 A1 | 8/2004 | Zawacki et al. | |
| 2004/0167478 A1 | 8/2004 | Mooney et al. | |
| 2004/0171997 A1 | 9/2004 | Wilson et al. | |
| 2004/0172003 A1 | 9/2004 | Wilson et al. | |
| 2004/0176739 A1 | 9/2004 | Stephens et al. | |
| 2004/0183305 A1 | 9/2004 | Fisher | |
| 2004/0186444 A1 | 9/2004 | Daly et al. | |
| 2004/0186445 A1 | 9/2004 | Raulerson et al. | |
| 2004/0193119 A1 | 9/2004 | Canaud et al. | |
| 2004/0243095 A1 | 12/2004 | Nimkar et al. | |
| 2005/0049555 A1 | 3/2005 | Moorehead et al. | |
| 2005/0080398 A1 | 4/2005 | Markel et al. | |
| 2005/0085765 A1 | 4/2005 | Voorhees | |
| 2005/0085794 A1 | 4/2005 | Denoth et al. | |
| 2005/0095891 A1 | 5/2005 | Schorn | |
| 2005/0096585 A1 | 5/2005 | Schon et al. | |
| 2005/0113805 A1 | 5/2005 | Devellian et al. | |
| 2005/0187535 A1 | 8/2005 | Wilson et al. | |
| 2005/0209572 A1 | 9/2005 | Rome et al. | |
| 2005/0209581 A1 | 9/2005 | Butts et al. | |
| 2005/0209584 A1 | 9/2005 | Rome | |
| 2005/0256461 A1 | 11/2005 | DiFiore et al. | |
| 2005/0261636 A1 | 11/2005 | Rome et al. | |
| 2005/0261664 A1 | 11/2005 | Rome et al. | |
| 2005/0261665 A1 | 11/2005 | Voorhees | |
| 2006/0015074 A1 | 1/2006 | Lynn | |
| 2006/0015086 A1 | 1/2006 | Rasmussen et al. | |
| 2006/0084929 A1 | 4/2006 | Eliasen | |
| 2006/0129134 A1 | 6/2006 | Kerr | |
| 2006/0276773 A1 | 12/2006 | Wilson et al. | |
| 2007/0016167 A1 | 1/2007 | Smith et al. | |
| 2007/0060866 A1 | 3/2007 | Raulerson et al. | |
| 2008/0009832 A1 | 1/2008 | Barron et al. | |
| 2008/0200901 A1 | 8/2008 | Rasmussen et al. | |
| 2009/0013944 A1 | 1/2009 | Re Fiorentin et al. | |
| 2009/0137944 A1 | 5/2009 | Haarala et al. | |
| 2010/0016838 A1 | 1/2010 | Butts et al. | |

FOREIGN PATENT DOCUMENTS

| | | | |
|---|---|---|---|
| EP | 0439263 A1 | 7/1991 | |
| EP | 0616817 | 9/1994 | |
| EP | 1240916 A1 | 9/2002 | |
| WO | 8401902 A1 | 5/1984 | |
| WO | WO-9421315 | 9/1994 | |
| WO | WO-9634645 | 11/1996 | |
| WO | 9722374 A1 | 6/1997 | |
| WO | 0023137 A1 | 4/2000 | |
| WO | WO-02058776 | 8/2002 | |
| WO | WO-03030960 | 4/2003 | |
| WO | WO-03030962 | 4/2003 | |
| WO | WO-03033049 | 4/2003 | |
| WO | 2006004943 A2 | 1/2006 | |
| WO | 2006066023 A2 | 6/2006 | |

OTHER PUBLICATIONS

Jun. 17, 2005 Written Opinion of the International Searching Authority in international application No. PCT/US2005/009150.
May 26, 2006 International Preliminary Report on Patentability in international application No. PCT/US2005/009150.
Camp, "Care of the Groshong Catheter", Oncol Nurs Forum, vol. 15, No. 6, 1988.
Delmore et al., "Experience with the Groshong Long-Term Central Venous Catheter", Gynecologic Oncology 34, 216-218 (1989).
Goldfarb et al., "Chronic Venous Access Bedside Placement Technique and Complications," Cancer Practice vol. 2, No. 4, pp. 279-283 (Jul./Aug. 1994).
Health Devices, "Hazard Report," vol. 25, Nos. 5-6, pp. 214-215, May-Jun. 1996.
Hull et al., "The Groshong Catheter: Initial Experience and Early Results of Imging-guided Placement," Cardiovascular Radiology 185:803-807 (1992).
Malviya et al., "Vascular Access in Gynecological Cancer Using the Groshong Right Atrial Catheter", Gynecological Oncology 33, 313-316 (1989).
Salem et al., "A New Peripherally Implanted Subcutaneous Permanent Central Venous Access Device for Patients Requiring Chemotherapy," Journal of Clinical Oncology, vol. 11, No. 11, p. 2181-2185 (Nov. 1993).
Twardowski et al., "Measuring Central Venous Structures in Humans: Implications for Central-Vein Catheter Dimensions," The Journal of Vascular Access 3:21-37 (2002).
U.S. Appl. No. 10/803,207, filed Mar. 18, 2004 Non-Final Office Action dated Sep. 19, 2005.
U.S. Appl. No. 10/803,207, filed Mar. 18, 2004 Notice of Allowance dated Apr. 21, 2006.
U.S. Appl. No. 10/803,279, filed Mar. 18, 2004, Advisory Action dated Aug. 22, 2007.
U.S. Appl. No. 10/803,279, filed Mar. 18, 2004, Final Office Action dated May 31, 2007.
U.S. Appl. No. 10/803,279, filed Mar. 18, 2004, Final Office Action dated Oct. 1, 2008.
U.S. Appl. No. 10/803,279, filed Mar. 18, 2004, Non-Final Office Action dated Apr. 2, 2009.
U.S. Appl. No. 10/803,279, filed Mar. 18, 2004, Non-Final Office Action dated Dec. 1, 2006.
U.S. Appl. No. 10/803,279, filed Mar. 18, 2004, Non-Final Office Action dated Jun. 5, 2006.
U.S. Appl. No. 10/803,279, filed Mar. 18, 2004, Non-Final Office Action dated Sep. 20, 2007.
U.S. Appl. No. 10/803,279, filed Mar. 18, 2004, Notice of Allowance dated May 28, 2009.
U.S. Appl. No. 10/803,512, filed Mar. 18, 2004 Advisory Action dated Oct. 16, 2008.
U.S. Appl. No. 10/803,512, filed Mar. 18, 2004 Final Office Action dated May 30, 2008.
U.S. Appl. No. 10/803,512, filed Mar. 18, 2004 Non-Final Office Action dated Jul. 22, 2009.
U.S. Appl. No. 10/803,512, filed Mar. 18, 2004 Non-Final Office Action dated May 24, 2010.
U.S. Appl. No. 10/803,512, filed Mar. 18, 2004 Non-Final Office Action Jan. 24, 2008.
U.S. Appl. No. 10/803,513, filed Mar. 18, 2004 Non-Final Office Action Jul. 25, 2008.
U.S. Appl. No. 10/803,513, filed Mar. 18, 2004 Notice of Allowance dated Jun. 12, 2009.
U.S. Appl. No. 11/076,564, filed Mar. 8, 2005 Advisory Action Nov. 16, 2006.
U.S. Appl. No. 11/076,564, filed Mar. 8, 2005 Final Office Action dated Aug. 25, 2006.
U.S. Appl. No. 11/076,564, filed Mar. 8, 2005 Final Office Action dated Jul. 27, 2007.
U.S. Appl. No. 11/076,564, filed Mar. 8, 2005 Non-Final Office Action dated Jan. 23, 2008.
U.S. Appl. No. 11/076,564, filed Mar. 8, 2005 Non-Final Office Action dated Mar. 9, 2006.
U.S. Appl. No. 11/076,564, filed Mar. 8, 2005 Non-Final Office Action dated Dec. 17, 2008.
U.S. Appl. No. 11/076,564, filed Mar. 8, 2005 Non-Final Office Action Feb. 9, 2007.
U.S. Appl. No. 11/076,564, filed Mar. 8, 2005 Notice of Allowance dated Jun. 17, 2009.
U.S. Appl. No. 11/096,553, filed Apr. 1, 2005 Advisory Action dated Aug. 1, 2007.
U.S. Appl. No. 11/096,553, filed Apr. 1, 2005 Final Office Action dated Feb. 27, 2007.
U.S. Appl. No. 11/096,553, filed Apr. 1, 2005 Non-Final Office Action dated Jan. 24, 2006.
U.S. Appl. No. 11/096,553, filed Apr. 1, 2005 Non-Final Office Action dated May 19, 2006.
U.S. Appl. No. 11/096,553, filed Apr. 1, 2005 Non-Final Office Action dated Oct. 10, 2007.

U.S. Appl. No. 11/096,553, filed Apr. 1, 2005 Notice of Allowance dated Mar. 25, 2008.
U.S. Appl. No. 11/122,303, filed May 2, 2005 Non-Final Office Action dated Jun. 8, 2009.
U.S. Appl. No. 11/122,303, filed May 3, 2005 Advisory Action dated Jul. 14, 2008.
U.S. Appl. No. 11/122,303, filed May 3, 2005 Final Office Action dated Apr. 30, 2008.
U.S. Appl. No. 11/122,303, filed May 3, 2005 Non-Final Office Action dated Jan. 20, 2010.
U.S. Appl. No. 11/122,303, filed May 3, 2005 Non-Final Office Action dated Sep. 13, 2007.
U.S. Appl. No. 11/122,303, filed May 3, 2005 Notice of Allowance dated Jul. 9, 2010.
U.S. Appl. No. 11/471,193, filed Jun. 20, 2006, Non-Final Office Action dated Jan. 14, 2010.
U.S. Appl. No. 11/471,193, filed Jun. 20, 2006, Notice of Allowance dated Jul. 26, 2010.
U.S. Appl. No. 12/106,704, filed Apr. 21, 2008 Final Office Action dated Apr. 15, 2010.
U.S. Appl. No. 12/106,704, filed Apr. 21, 2008 Non-Final Office Action dated Apr. 27, 2009.
U.S. Appl. No. 12/106,704, filed Apr. 21, 2008 Non-Final Office Action dated Oct. 22, 2009.
Vesely, "Central Venous Catheter Tip Position: A Continuing Controversy," JVIR vol. 14, No. 5, pp. 527-534 (May 2003).

\* cited by examiner

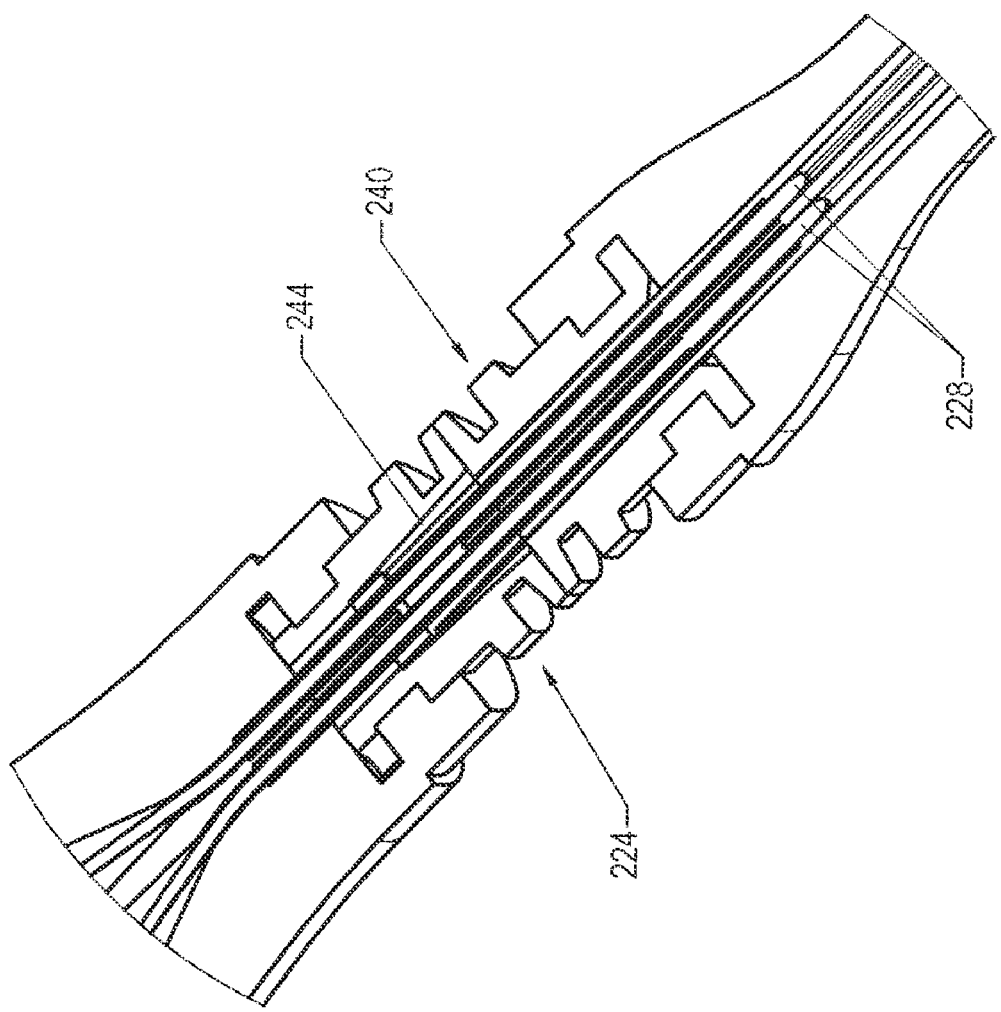

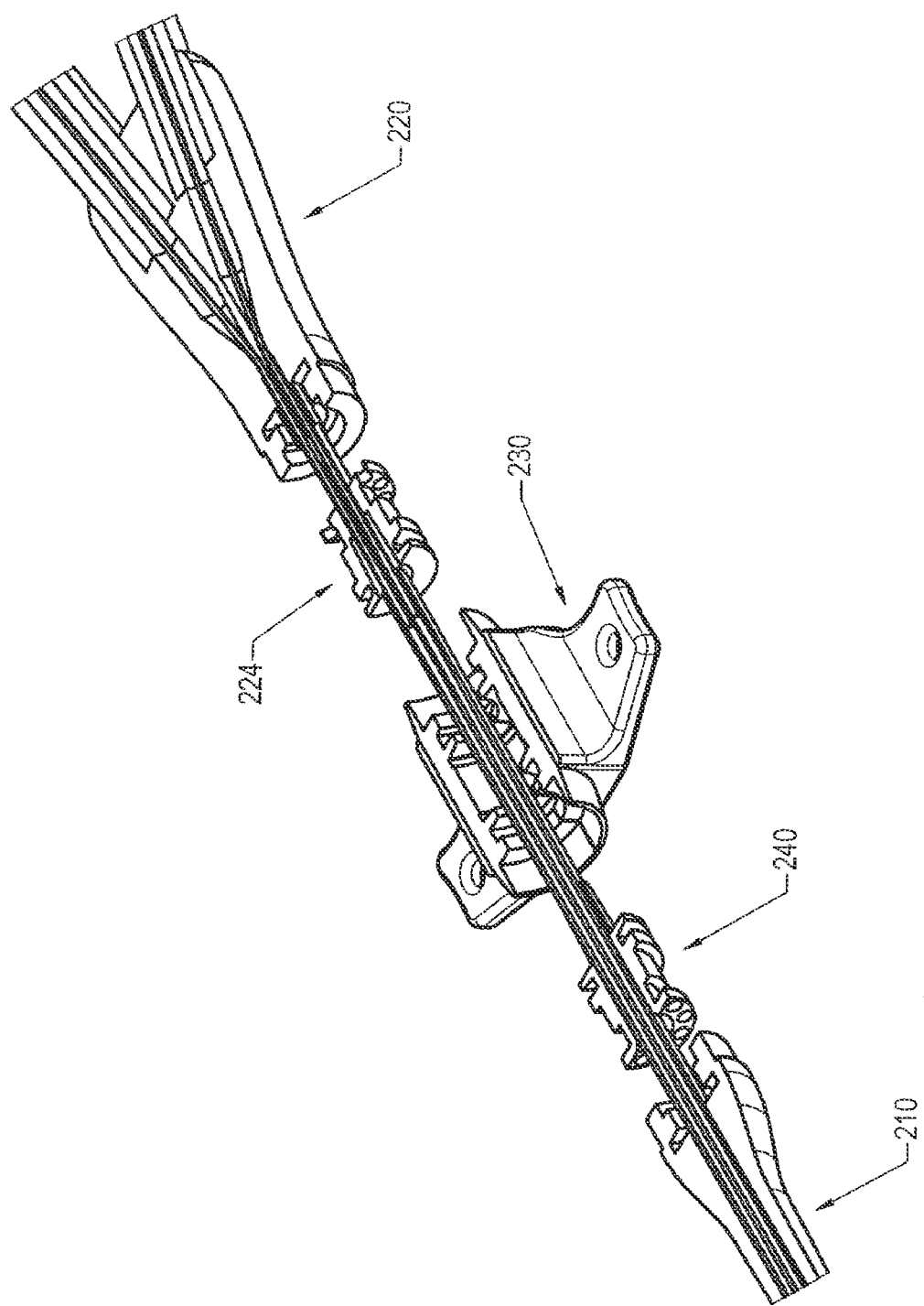

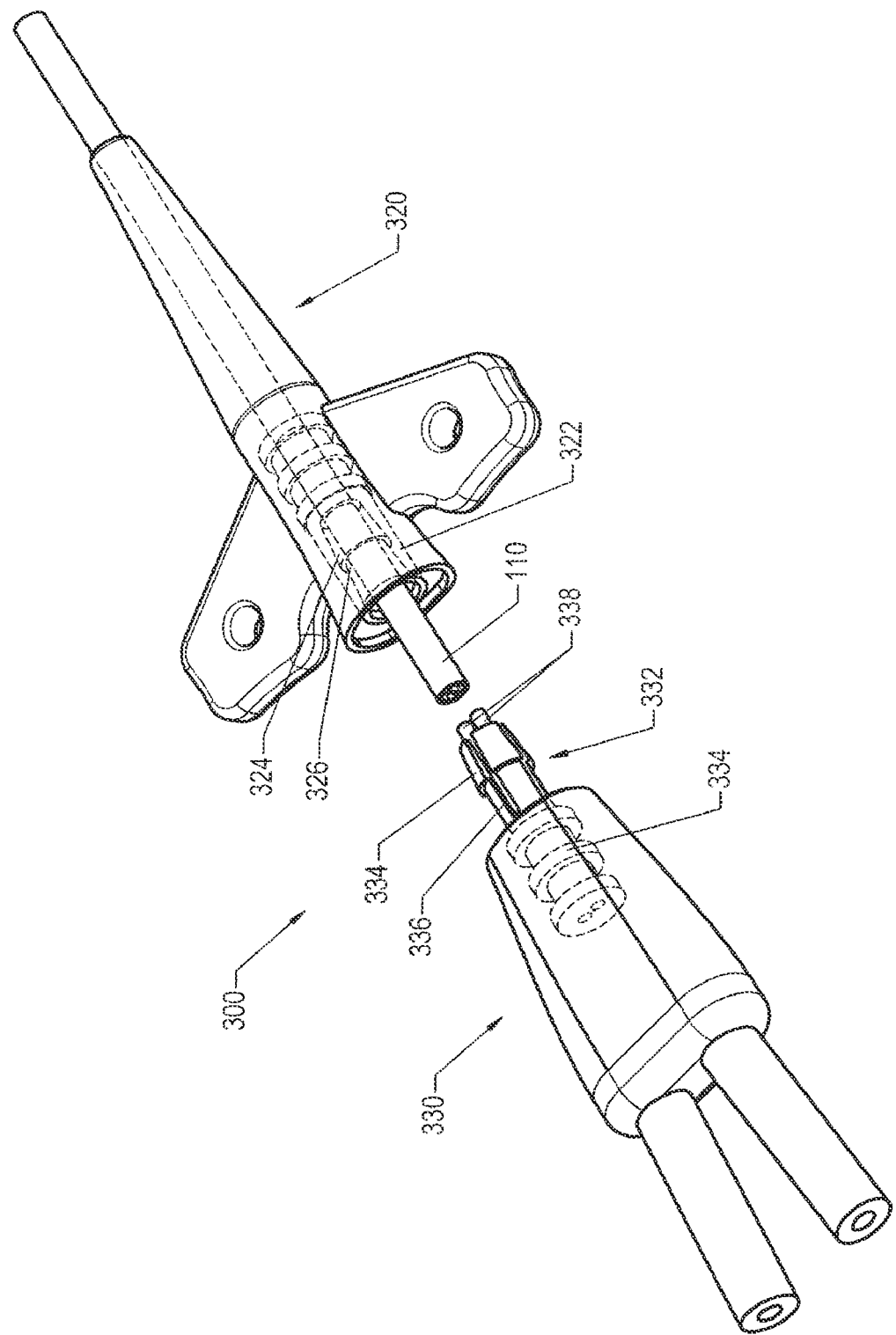

CONNECTOR SYSTEM FOR A PROXIMALLY TRIMMABLE CATHETER

PRIORITY

This application is a division of U.S. patent application Ser. No. 10/803,513, filed Mar. 18, 2004, now U.S. Pat. No. 7,594,911, which is incorporated by reference in its entirety into this application.

BACKGROUND OF THE INVENTION

It is common to use an implanted catheter to repeatedly access the vascular system of a patient and with the catheter perform repeated therapeutic medical activity. Such therapeutic activity could include the intermittent or continuous infusion of medication and fluids, the periodic sampling of blood, or the continuous withdrawal and return of blood for processing outside of the body of the patient. The catheters used in these activities are referred to as vascular access catheters.

Before any therapeutic activity can actually commence, however, the vascular access catheter must be implanted in the body of the patient with the distal tip of the catheter residing at the location in the vascular system at which an intended therapeutic activity is appropriate. Typically, most of the length of an implanted vascular access catheter resides within blood vessels of the vascular system, extending from the distal tip of the catheter to a location in the vascular system at which the catheter, by traversing a puncture or incision formed through a wall of the blood vessel in which the catheter is disposed, enters into the surrounding subcutaneous tissue of the patient. The location at which this occurs is referred to as a venipuncture site. Venipuncture sites are classified on the basis of the position of a venipuncture site in relation to the center of the body of the patient. Central venipuncture sites are those that enter the vasculature through the jugular or subclavian veins. Peripheral venipuncture sites typically enter the basilic or cephalic veins of the upper or lower arm. The freedom to select among venipuncture sites is determined largely on catheter size and vein size. Vein size is dependent on patient size and on location within the body, with peripheral veins being smaller than central veins.

Proximal of the venipuncture site, the implanted catheter extends through the subcutaneous tissue of the patient to emerge through the skin at a location that is referred to as the skin exit site. Most skin exit sites are chosen as being locations at which the proximal end of the implanted catheter can be easily manipulated by medical personnel. Favored among such locations are the neck, the region about the collar bone or chest wall, the upper leg, the upper arm, and the forearm. Occasionally, the skin exit site is somewhat removed from the venipuncture site. Then a significant portion of the length of the implanted catheter must be embedded in the subcutaneous tissue of the patient in a surgically created tunnel that extends from the venipuncture site to the skin exit site. In all instances, a portion of the proximal end of an implanted catheter must remain outside of the body of the patient. It is this portion of an implanted catheter, from the proximal end thereof to the skin access site, that is referred to as the extracorporeal portion of the implanted catheter.

The extracorporeal portion of an implanted catheter must be capable of being selectively coupled to and uncoupled from the tubing and medical equipment outside the body of the patient that are required for therapeutic activity. Accordingly, the proximal end of virtually all vascular access catheters terminates in a catheter coupling hub that can be secured in fluid communication with such tubing and medical equipment, or can be capped, valved, or clamped closed between periods of actual use. Due to the variation in length of catheter that is required to traverse the subcutaneous and intravascular route from implanted tip location to skin exit site, it often becomes necessary to trim the catheter to an appropriate length. Traditionally, it is the distal end of the catheter that is trimmed as opposed to the proximal end for a number of reasons, including the desire to provide accurate positioning of a pre-connected proximal suture wing hub in a desired location near the venipuncture site. In particular, clinicians are increasingly showing a preference for a stepped-taper or reverse-taper of the hub to be inserted partially into the venipuncture site to affect tamponade and reduce site bleeding.

Trimming the catheter to an appropriate length is particularly advantageous with respect to peripherally inserted central catheters (PICCs) where precise central venous catheter tip placement at the right atrial (RA), superior vena cava (SVC) junction is imperative to prevent potential thrombosis, traumatic or functional complications. Many types of catheters, however, cannot be distally trimmed due to the special configuration thereof, including, for example, dual lumen catheters with a pre-staggered tip, soft tip catheters, catheters with valved distal ends, etc. In the case of such catheters, a pre-connected hub at the proximal end of the catheter cannot be accurately located at the venipuncture site and, consequently, some length of catheter extends therefrom. This excess catheter length often presents difficulty in dressing the catheter and exposes the catheter to potential damage. Moreover, it is not possible in the placement of catheters having preformed distal tips to achieve tamponade at the venipuncture site.

Whether or not the catheter has a preformed distal tip, it is advantageous to be able to trim a catheter at its proximal end prior to connection to a coupling hub or other extracorporeal medical equipment because proximal trimming enables physicians to keep inventory low (as several different catheter lengths are unnecessary) and each catheter placed can be customized to the exact length optimal for patient comfort and operability of the catheter. As a result, many types of connection systems have been proposed to couple a proximal end of a catheter to a medical device.

With particular reference to a catheter that has a been subcutaneously placed, in which an extracorporeal portion is to be connected to a coupling hub, systems such as that shown in FIG. 1 have been traditionally utilized. As shown, a catheter 20 is attached to a coupling hub 12 through three preassembled pieces. The proximal end of the catheter 20 is slid through strain relief sleeve 18, distal coupling 16 and compression sleeve 14. The proximal end of the catheter 20 is then slid over the cannula of coupling hub 12. Distal coupling 16 is snapped into coupling hub 12, exerting pressure against compression sleeve 14, which in turn retains catheter 20 on the cannula coupling hub 12. While such a connection system may be adequate for providing a secure connection, assembly can prove problematic due to the small size of the pieces involved as well as the extremely limited space with which the physician typically has to work. Moreover, the manufacture of several different pieces may lengthen the time to manufacture, as well as the cost associated therewith.

As mentioned above, in some instances it is preferable to partially insert a catheter hub into the venipuncture site. However, a system has not been previously proposed that will permit precise placement of the non-trimmed distal tip of the catheter subcutaneously while also providing the ability for the proximal hub to be partially inserted into the venipuncture site. Moreover, whereas prior art systems for proximally trimmable single lumen catheters have been proposed, such as depicted in FIG. 1, there has not to date been proposed a system for proximally trimmable externalized dual lumen catheters.

Accordingly, it is an object of the present invention to provide a catheter connector system, which safely and effectively connects a proximal end of a catheter to extracorporeal medical equipment, following placement of the distal end of the catheter in a patient. It is a further object of the present invention to provide a catheter connector system that permits venipuncture tamponade, that reduces assembly time of an associated suture wing, that improves robustness of the externalized catheter by eliminating unprotected catheter portions, that provides the functionality of a repair kit, and that provides a proximally trimmable design for a dual-lumen catheter.

Various other objectives and advantages of the present invention will become apparent to those skilled in the art as more detailed description is set forth below.

BRIEF SUMMARY OF THE INVENTION

The present invention is directed to a catheter connector system for a subcutaneously placed catheter. The catheter connector system permits proximal trimming of the placed catheter, which is a procedure that provides numerous advantages over traditional methods of trimming catheter distal ends prior to implantation. Further, the catheter connector system of the present invention facilitates precise positioning of both distal and proximal ends of a catheter, which provides enhanced functionability and patient comfort.

In one embodiment of the present invention, a catheter connector system for a catheter comprises a boot comprising a tapered outer wall having a diameter that decreases toward a distal end thereof, said outer wall enclosing a longitudinally extending lumen, wherein said boot lumen is sized to prevent axial movement of said catheter when said catheter is positioned therein, and a bifurcation assembly, comprising at least one extension leg extending from a proximal end thereof and at least one stem extending from a distal end thereof, wherein said at least one stem is configured to be received into a lumen of said catheter.

In another embodiment of the present invention, a kit for connecting a catheter to extracorporeal medical equipment comprises a boot comprising a tapered outer wall having a diameter that decreases toward a distal end thereof, said outer wall enclosing a longitudinally extending lumen, wherein said boot lumen is sized to prevent axial movement of said catheter when said catheter is positioned therein, a bifurcation assembly, comprising at least one extension leg extending from a proximal end thereof and at least one stem extending from a distal end thereof, wherein said at least one stem is configured to be received into a lumen of said catheter, and a dilator comprising a shaft having an outer wall enclosing a longitudinally extending lumen, said shaft configured to expand said boot lumen when positioned therein, said dilator lumen configured for slideable movement over said catheter.

In yet another embodiment of the present invention, a proximally trimmable catheter system comprises a catheter comprising at least one lumen, a boot comprising a tapered outer wall having a diameter that decreases toward a distal end thereof, said outer wall enclosing a longitudinally extending lumen, wherein said boot lumen is sized to prevent axial movement of said catheter when said catheter is positioned therein, a bifurcation assembly, comprising at least one extension leg extending from a proximal end thereof and at least one stem extending from a distal end thereof, wherein said at least one stem is configured to be received into a lumen of said catheter, and a dilator comprising a shaft having an outer wall enclosing a longitudinally extending lumen, said shaft configured to expand said boot lumen when positioned therein, said dilator lumen configured for slideable movement over said catheter.

In still another embodiment of the present invention, a catheter connector system for an implanted catheter comprises a boot comprising a tapered outer wall, having a diameter that decreases toward a distal end thereof and enclosing a longitudinally extending lumen, and a first connector member positioned at a proximal end thereof, a bifurcation assembly, comprising at least one extension leg extending from a proximal end thereof and a second connector member positioned at a distal end thereof, said second connector member having at least one stem extending therefrom, said stem being configured to be received into a lumen of said catheter, and a clamp configured to lock around said first and second connector members.

In yet another embodiment of the present invention, a kit for connecting a catheter to extracorporeal medical equipment comprises a boot comprising a tapered outer wall, having a diameter that decreases toward a distal end thereof and enclosing a longitudinally extending lumen, and a first connector member positioned at a proximal end thereof, a bifurcation assembly, comprising at least one extension leg extending from a proximal end thereof and a second connector member positioned at a distal end thereof, said second connector member having at least one stem extending therefrom, said stem being configured to be received into a lumen of said catheter, a clamp configured to lock around said first and second connector members, and at least one obturator, having a rounded tip, positioned through said extension leg and said stem.

These and other embodiments, features and advantages of the present invention will become more apparent to those skilled in the art when taken with reference to the following more detailed description of the invention in conjunction with the accompanying drawings that are first briefly described.

BRIEF DESCRIPTION OF THE DRAWINGS

FIG. 14 is a longitudinal cross-sectional view of a partially assembled catheter connector system employing the connector member of FIG. 13.

FIG. 15 is an exploded cross-sectional view of a catheter connector system employing the connector member of FIG. 13.

FIG. 16 is a perspective view of an alternate embodiment of a catheter connector system according to the present invention.

DETAILED DESCRIPTION OF THE INVENTION

Figure 1:
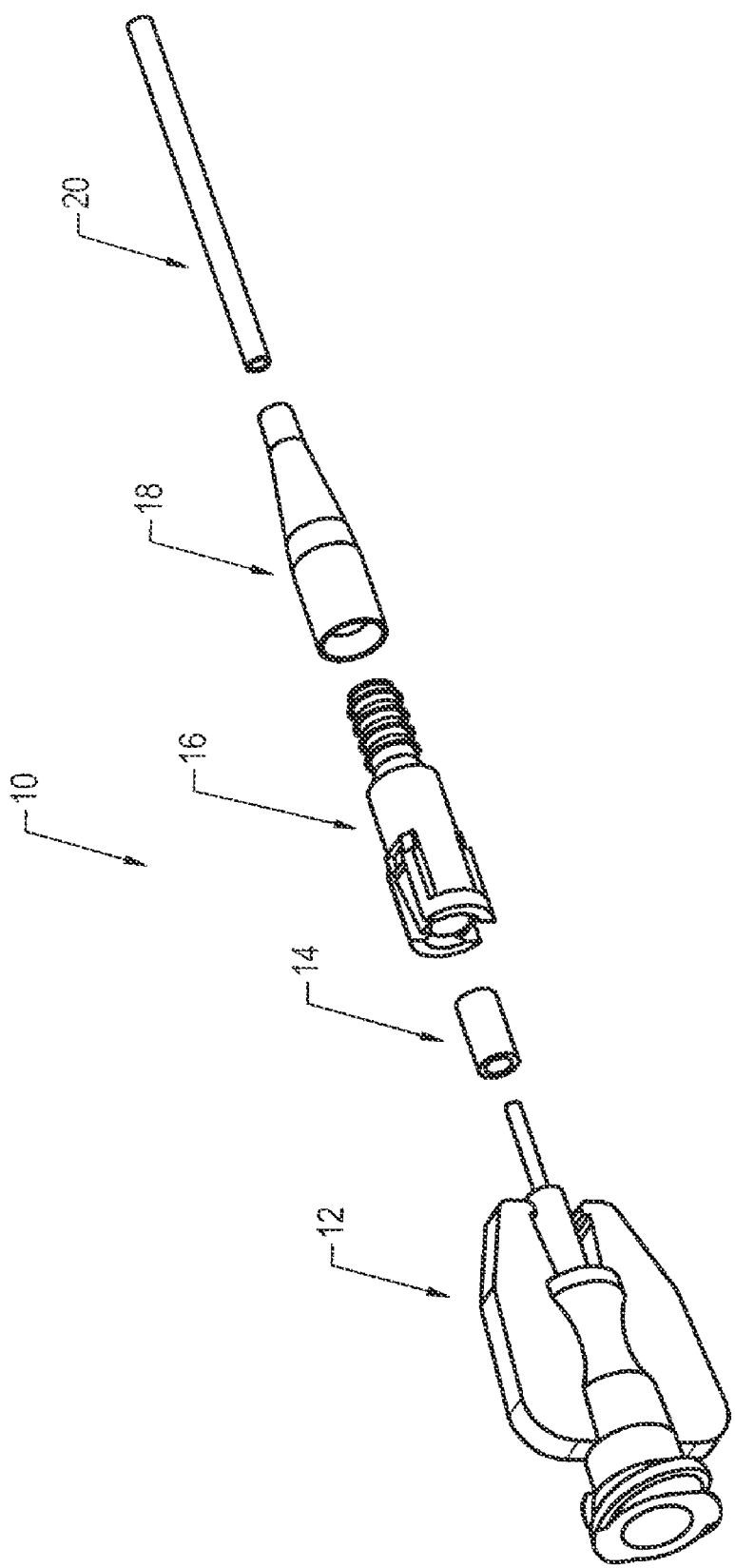
FIG. 1 is an exploded view of a prior art catheter connector system.

The following detailed description should be read with reference to the drawings, in which like elements in different drawings are identically numbered. The drawings, which are not necessarily to scale, depict selected preferred embodiments and are not intended to limit the scope of the invention. The detailed description illustrates by way of example, not by way of limitation, the principles of the invention. This description will clearly enable one skilled in the art to make and use the invention, and describes several embodiments, adaptations, variations, alternatives and uses of the invention, including what is presently believed to be the best mode of carrying out the invention.

The present invention is directed to a catheter connector system for connecting a catheter to extracorporeal medical equipment. In the embodiments and examples that follow, reference will be made to a catheter connector for a catheter that has been trimmed proximally, following placement thereof in the body of a patient. However, it should be understood that the present invention is not limited to such uses and instead is applicable to any application that requires the connection of a catheter to separate medical equipment as would be apparent to one of skill in the art. Moreover, when discussing the catheter connectors of the present invention in terms of attachment to a patient, it should be understood that attachment can be direct through suturing, medical tape, or other means, or indirect through the use of a StatLock® or other intermediary device.

In one embodiment according to the present invention, a catheter connector system 100 is illustrated in FIGS. 2-10. The catheter connector system 100 includes two primary components, a boot 120 and a bifurcation assembly 130, and is configured for attachment to a catheter 110 to provide a proximal connection for the introduction and/or withdrawal of fluids thereto. The catheter connector system 100 as illustrated is configured as a two-piece system, which can be assembled by the clinician upon placement of a catheter. It should be appreciated that although the embodiments shown are directed to a dual lumen catheter, similar embodiments directed to single lumen and triple lumen catheters are contemplated (as well as other multi-lumen catheters). More particularly, while the catheter 110 and bifurcation assembly 130 are illustrated in a dual-lumen configuration, the present invention is equally directed to a single lumen configuration, having a single lumen catheter and assembly, and to a triple or multi-lumen configuration, having a triple or multi-lumen catheter and assembly.

The catheter connector of the present invention can be used for a variety of different types of catheters, such as peripherally inserted central catheters (PICCs), having small or large diameters. In one embodiment, catheter connector system 100 is configured for a PICC, ranging from 3 Fr to 7 Fr in size. While certainly many different materials could be used for each of the primary components of the catheter connector system 100 and catheter 110, examples of possible materials are polyurethane and silicone (i.e., a soft biocompatible elastomeric material) for the catheter 110 and the boot 120, and either a soft elastomeric material or a hard plastic material for the bifurcation assembly 130.

Figure 2:
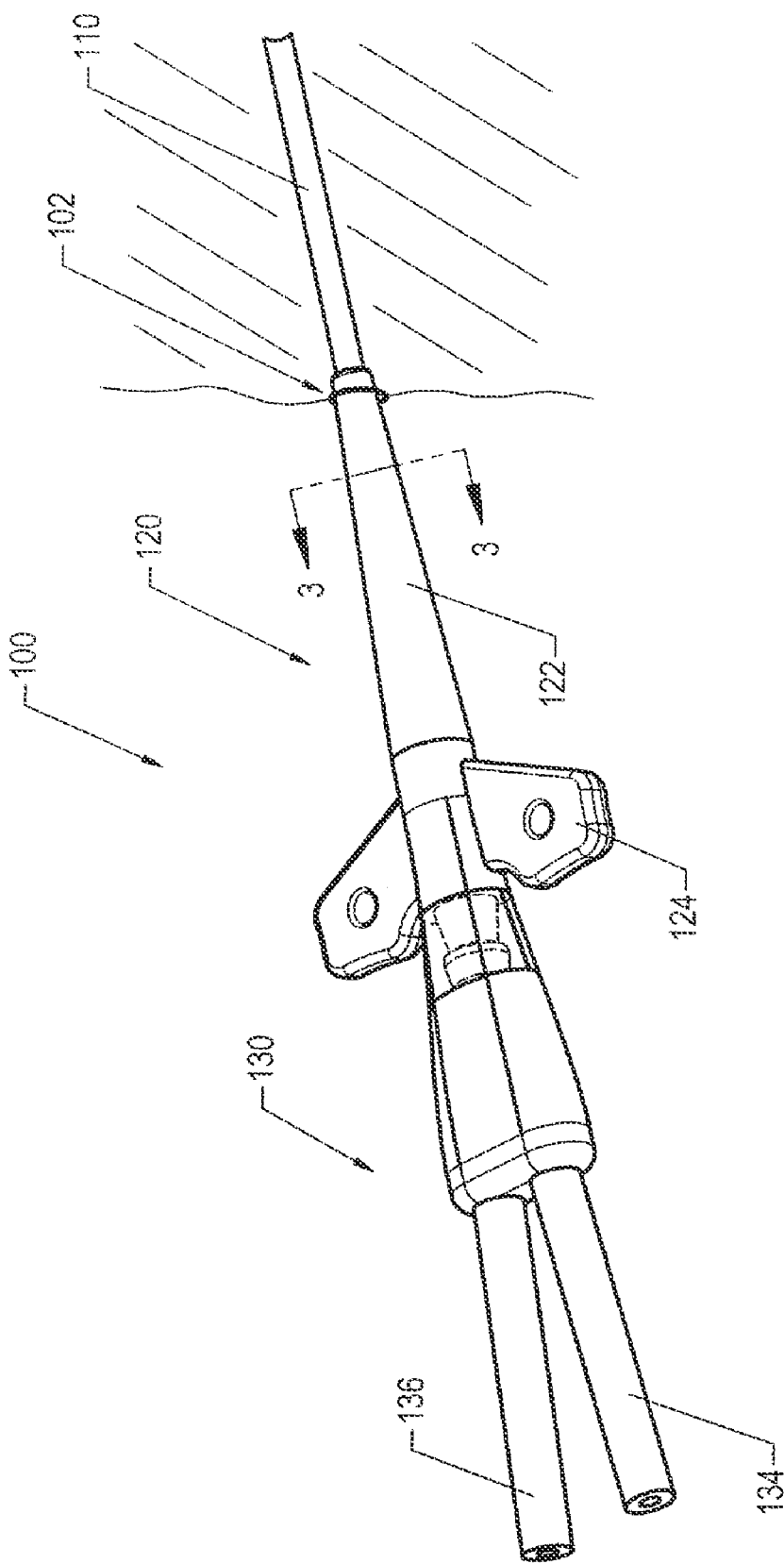
FIG. 2 is a perspective view of a catheter connector system according to the present invention.
Figure 3:
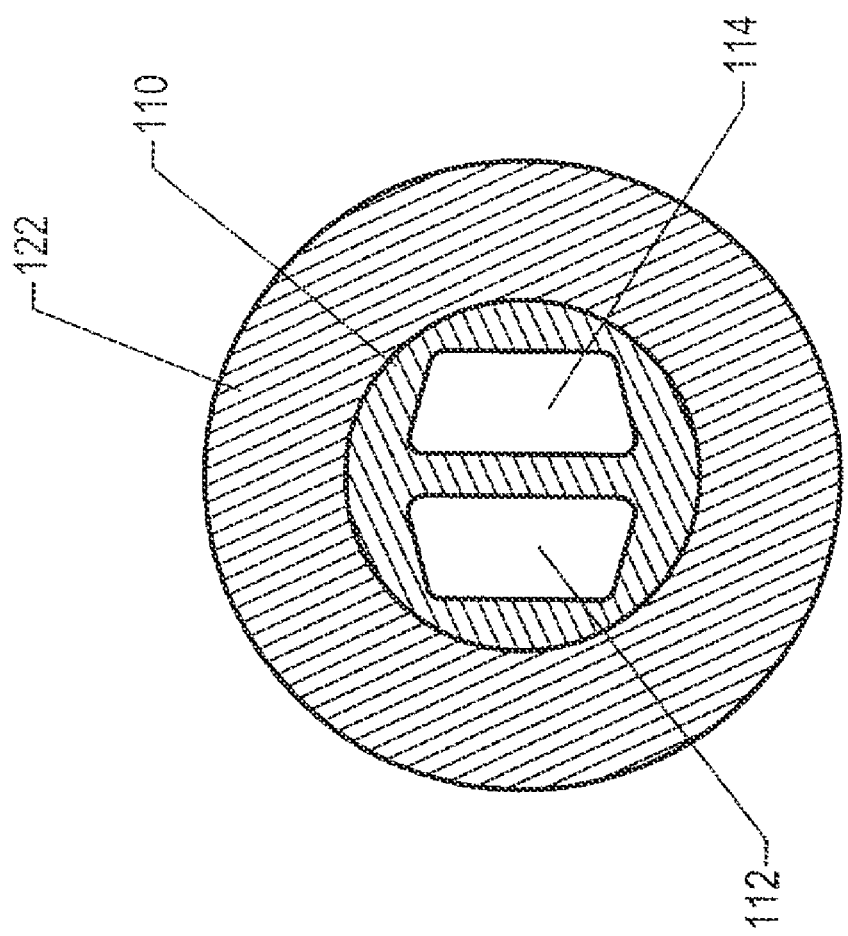
FIG. 3 is a cross-sectional view of the boot and catheter of FIG. 2, taken along line 3-3.

Referring to FIG. 2, the bifurcation assembly 130 includes extension leg tubes 134, 136, which are in fluid communication with catheter lumens 112, 114 (FIG. 3) when catheter connector system 100 is fully assembled. The boot 120 includes a main body portion 122 and a pair of suture wings 124 that are configured for attachment to the skin of a patient or a StatLock® or similar device to stabilize the catheter connector system 100. As shown in the cross-sectional view in FIG. 3, the catheter 110 within the boot 120 has lumens 112, 114 with a trapezoidal cross-sectional shape. While certainly other cross-sectional shapes are possible, the trapezoidal shape may be advantageous to prevent collapse due to the force exerted on the catheter 110 by the boot 120.

Figure 4:
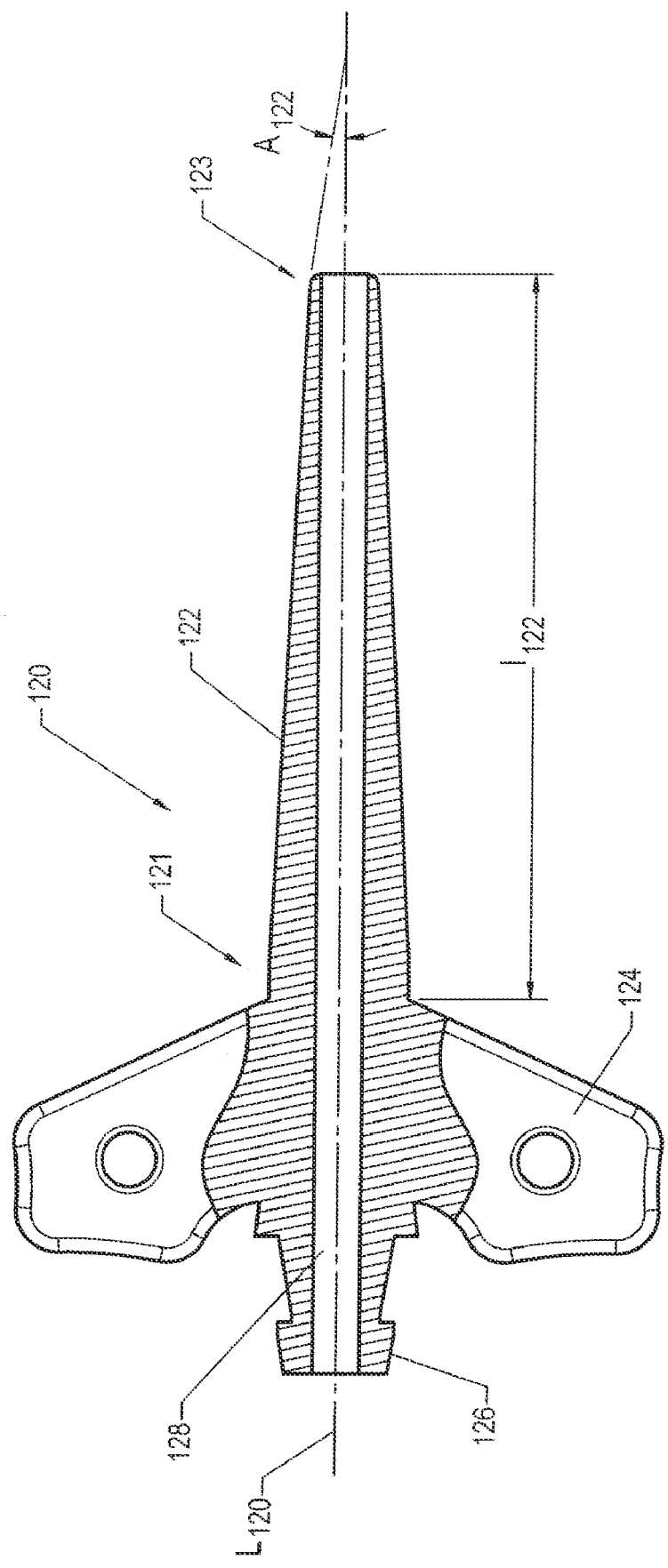
FIG. 4 is a partial cut-away view of a boot portion of the catheter connector system of FIG. 2.

FIG. 4 illustrates in partial cut-away view the boot 120. In this isolated view of the boot 120, a proximal coupling section 126 can be seen comprising a barbed end. Of course, coupling section 126 can take on a variety of forms, depending on the form of the associated coupling section of the bifurcation assembly 130, such that the coupling sections together provide a tight connection that will withstand forces associated with the infusion and/or withdrawal of fluid from a patient. The main body portion 122 of boot 120 is fashioned with a reverse-taper or stepped-taper, meaning that the diameter at the proximal end 121 is greater than the diameter at the distal end 123. This is advantageous because the smaller diameter distal end 123 can be partially inserted into the venipuncture site 102, as shown in FIG. 2, to achieve venipuncture tamponade and reduce site bleeding. Although the taper of main body portion 122 is shown as being very slight with respect to the longitudinal axis $L_{120}$ of the boot 120, forming an angle $A_{122}$ therewith, the preferred range is between approximately 1 to 45 degrees with larger tapers being equally within the scope of the present invention.

The main body portion 122 includes a section distal the suture wings 124, having a length $l_{122}$ that in one embodiment is in the range of approximately 2.0 cm to 5.0 cm. The boot 120 is formed with a throughgoing lumen 128 and may have a diameter slightly smaller than the diameter of the outer wall of the catheter 110 to create an interference fit therewith. Although certainly various diameters are possible for the lumen 128 and the outer wall of the catheter 110, in one embodiment the diameter of the lumen 128 is in the range of approximately 0.50 mm to 4.0 mm, while the diameter of the outer wall of the catheter 110 is approximately 0.55 mm to 4.4 mm. The lumen 128 is also sized to receive a dilator, which is used to place the boot 120 over the catheter 110 and into the venipuncture site 102.

Figure 5:
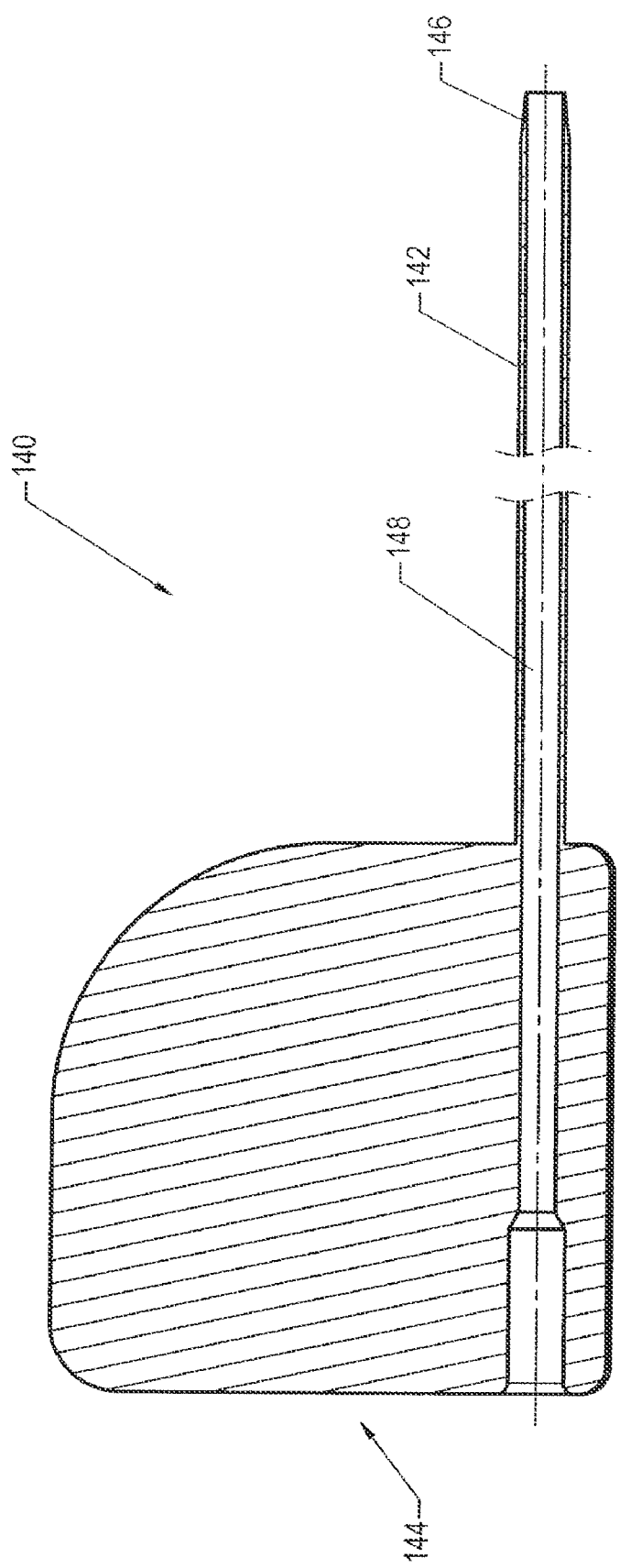
FIG. 5 is a cross-sectional view of a dilator used according to the present invention.

FIG. 5 illustrates a dilator 140 in cross-section, the dilator 140 including a shaft 142 that has a transition section 146 at a distal end thereof, which is tapered to form a smooth transition for insertion percutaneously into the venipuncture site. In addition, the tip of the transition section 146 may be rounded (e.g., via radio frequency means, thermal means, etc.) The shaft 142 has an outer diameter that is larger than lumen 128 of boot 120 in order to dilate the lumen 128 and provide an interference fit for a tight, smooth transition into the venipuncture site. The dilator 140 also has a throughgoing lumen 148, which can be slightly larger than the diameter of the outer wall of the catheter 110 to allow slideable movement therealong. In one embodiment, the dilator lumen 148 is at least 0.025 mm greater than the diameter of the outer wall of the catheter 110. In addition, the dilator 140 has a handle 144 (FIG. 6) positioned at the distal end thereof, the handle 144 having a fin 143 and a base 145, which together facilitate the handling of the dilator 140. The fin 143, base 145, or both may additionally be equipped with gripping sections to further facilitate the handling of the dilator 140. The dilator should be formed of a material exhibiting sufficient columnar and radial strength to prevent compression or time/thermal creep and allow advancement into the boot and removal therefrom (e.g., polyurethane, polytetrafluoroethylene (PTFE) and high density polyethylene (HDPE)). In one embodiment, the outer surface of the shaft 142 is lubricated to facilitate removal from the boot 120.

Figure 6:
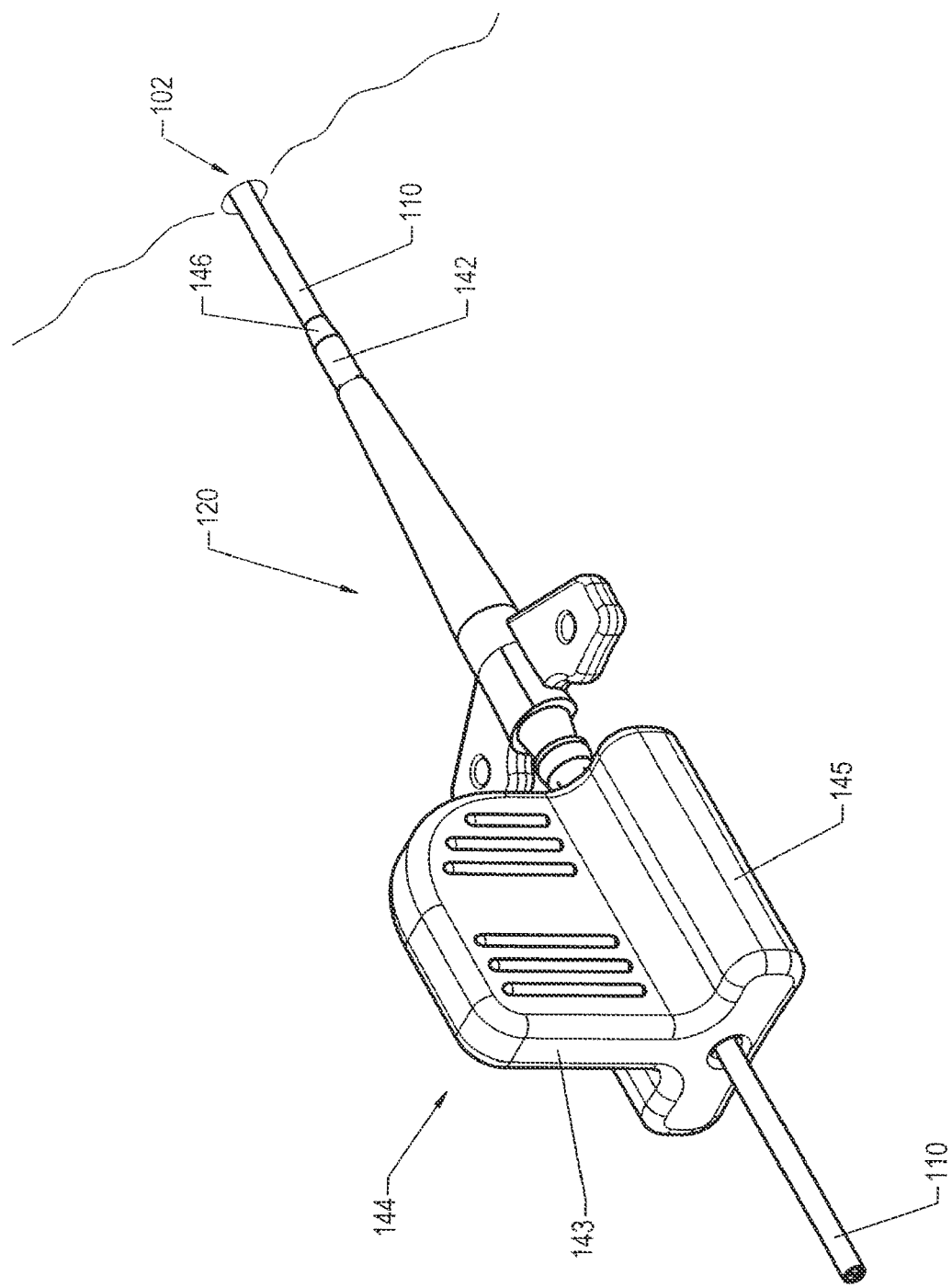
FIG. 6 is a perspective view of a dilator and boot according to the present invention being positioned over the proximal end of a placed catheter.
Figure 7:
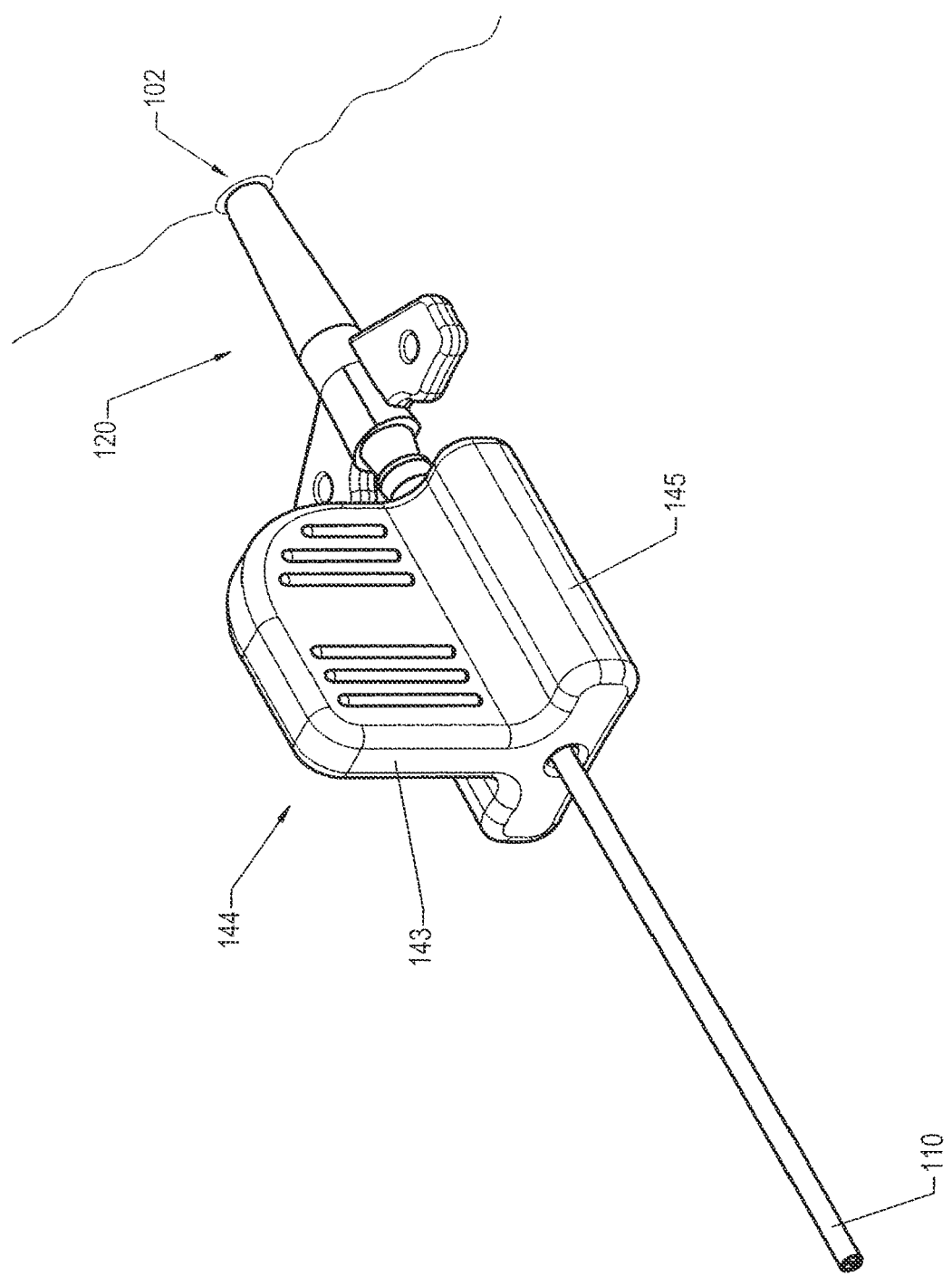
FIG. 7 is a perspective view of a dilator and boot according to the present invention being partially inserted into a venipuncture site.
Figure 8:
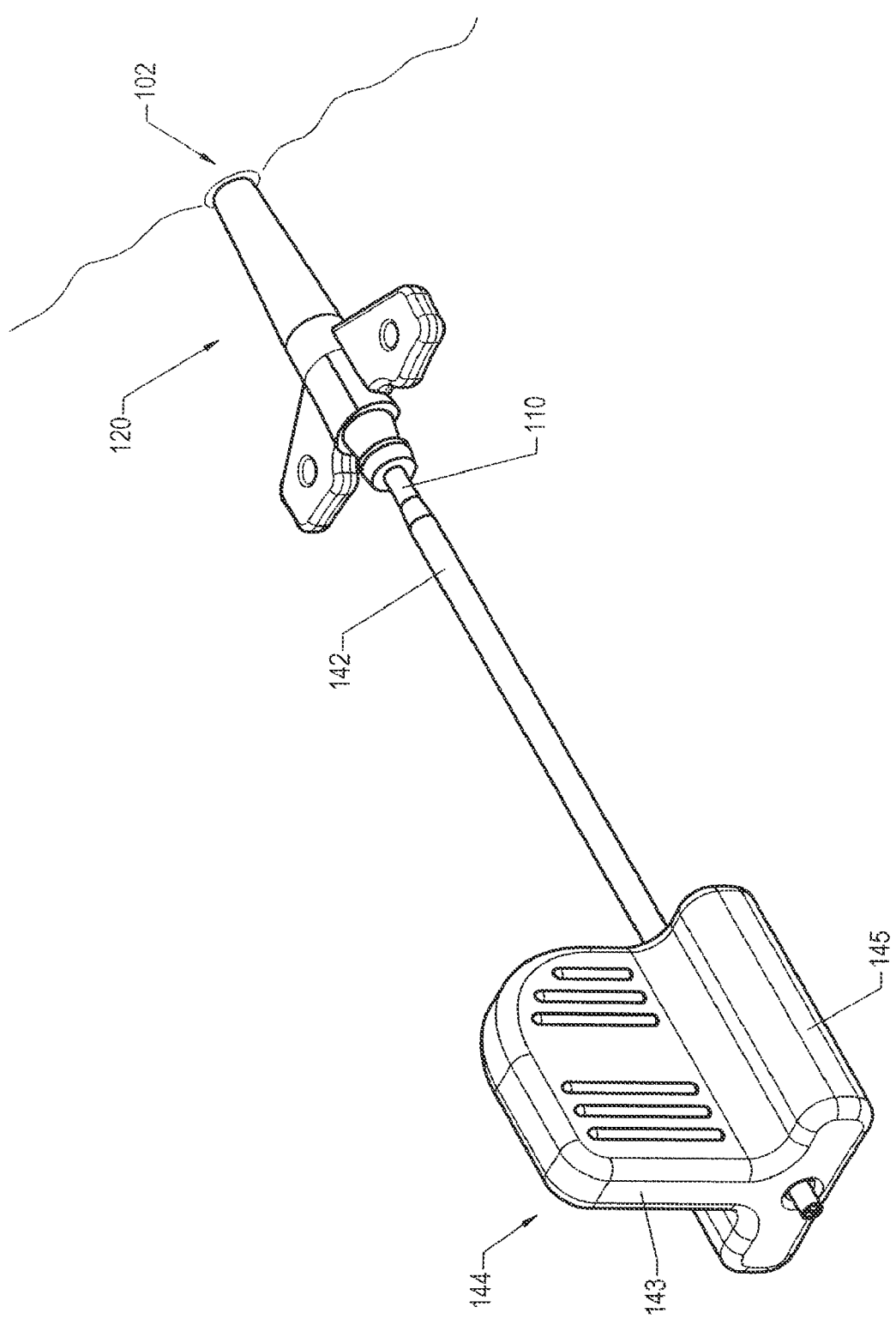
FIG. 8 is a perspective view of a dilator being removed from a boot.
Figure 9:
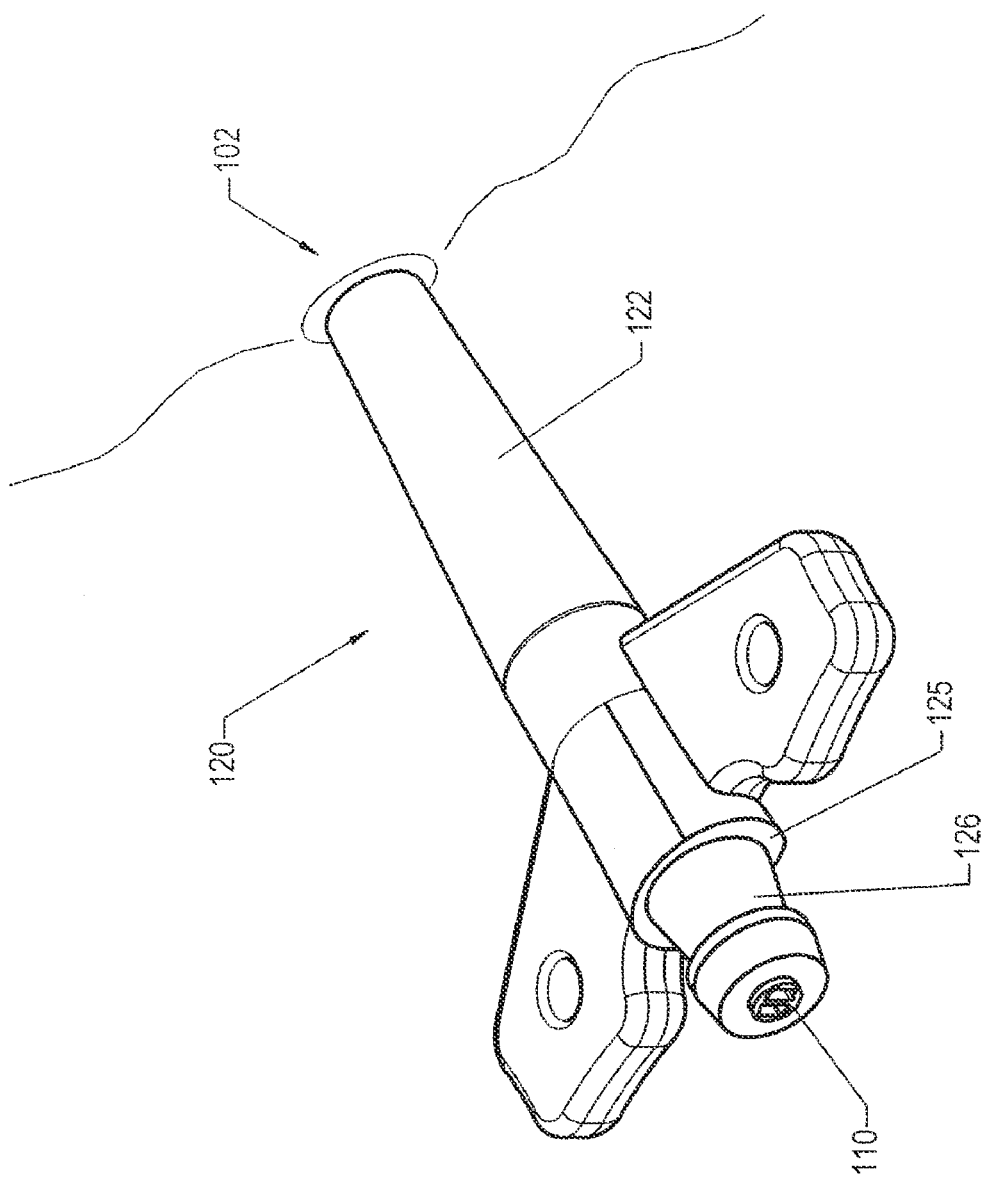
FIG. 9 is a perspective view of a boot placed partially into the venipuncture site with the proximal end of the catheter extending therefrom.

FIGS. 6-9 illustrate, in sequence, steps according to the present invention for inserting the boot into the venipuncture site. Referring to FIG. 6, the venipuncture site 102 has been established and the catheter 110 has been advanced to a central location, a length of the catheter 110 extending from the venipuncture site 102. The shaft 142 of the dilator 140 has been pressed into the lumen 128 of the boot 120 (generally performed at the place of manufacture, but can take place on site) and the combination is slid over the catheter 110, the lumen 148 of the dilator 140 receiving the catheter 110 therethrough. FIG. 7 shows the next step as the boot 120 and dilator 140 are pressed into the venipuncture site 102, with the catheter 110 extending from the proximal end of the dilator 140. Both the reverse-taper of the boot 120 and the transition section 146 of the dilator 140 enable a smooth advancement into the venipuncture site 102. As stated above, the reverse-taper configuration of the boot shaft 122 provides a tight fit into the venipuncture site and reduces blood loss therethrough. The dilator 140 is then removed from the boot 120, which is held in place in the venipuncture site, as depicted in FIG. 8. As the dilator 140 is removed from the lumen 128 of the boot 120, the lumen 128, which was previously expanded due to the larger diameter of the dilator shaft 142, contracts and forms a tight fit with the catheter 110 remaining therein. Thereafter, the proximal length of the catheter 110 extending from the now placed boot 120 is trimmed (e.g., using medical scissors, a scalpel or other cutting tool) so that the proximal end of the trimmed catheter 110 is flush with the opening in the proximal end of the boot 120, resulting in the entire external length of the catheter 110 being supported and protected by the boot 120, as illustrated in FIG. 9.

Figure 10:
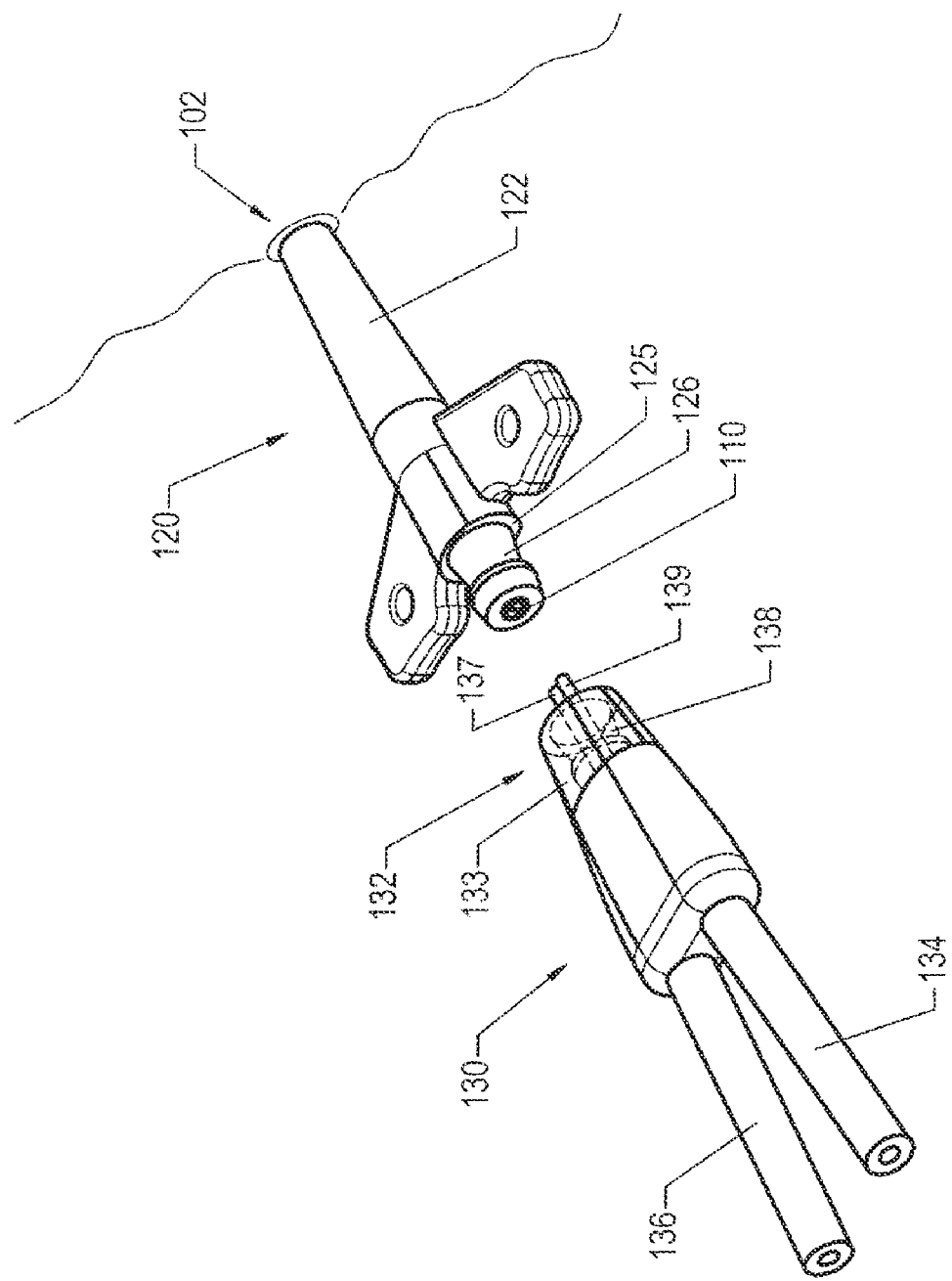
FIG. 10 is a perspective view of a pre-assembled view of the boot and bifurcation assembly of the catheter connector system of FIG. 2.

Referring now to FIG. 10, the attachment of the bifurcation assembly 130 is described. Bifurcation assembly 130 includes a coupling section 132, which is configured for attachment to the proximal coupling section 126 of the boot 120 to provide a securing connection thereto. The coupling section 132 includes a pair of stems 137, 139, which are shaped and sized to fit tightly within lumens 112, 114 of catheter 110 to provide a fluid tight connection between the boot 120 and the bifurcation assembly 130. In one embodiment, the stems are made of metal, although certainly other non-metal materials are also possible. Immediately surrounding the stems 137, 139 is a hood 138, which is configured and shaped to tightly receive proximal coupling section 126 of the boot 120. Surrounding both stems 137, 139 and hood 138 is a cover 133, which abuts a shoulder 125 at the proximal end 121 of the main body portion 122 upon assembly and has a diameter approximately the same as the diameter thereof. The stems 137, 139 extend beyond the cover 133 to enable initial engagement with the catheter lumens 112, 114 prior to the remainder of the coupling section 132 coming into contact with the proximal coupling section 126.

The bifurcation assembly 130 is assembled onto the boot 120 by sliding the stems 137, 139 into the respective lumens 112, 114 of the catheter 110, while providing pressure to the boot 120 to ensure a stationary position. To facilitate this insertion process and prevent damage to the catheter, round-nosed obturators, which are described in more detail below, may be utilized. As the stems 137, 139 are received into the lumens 112, 114, the hood 138 receives the barbed portion of the proximal coupling section 126. The assembly is complete when the cover 133 comes into contact with the shoulder 125 and the proximal coupling section is locked within the hood 138. The connection between the bifurcation assembly 130 and the boot 120 can be of several different varieties. In one embodiment, the pressing of the proximal coupling section 126 into the hood 138 results in both an audible and tactile indication that the connection is complete. The connection may be permanent, such as the embodiment shown in FIG. 10, or alternatively a releasable locking mechanism can be provided. The assembled catheter connector system 100, as illustrated in FIG. 2, provides a secure, fluid-tight connection system that is streamlined and is capable of attachment to the patient. Following complete assembly of the catheter connector system 100, the catheter is flushed to assure patency and to examine the connection for leaks. Finally, the suture wings 124 are secured to either the skin of the patient or a StatLock® or similar device.

Catheter connector system 300 is illustrated in FIG. 16 and is similar to catheter connector system 100. Catheter connector system 300 includes a bifurcation assembly 330 having a distal coupling section 332 configured to be received within a proximal receiving portion 322 of a boot 320. The distal coupling section 332 is comprised of an anchoring portion 334, an enlarged head portion 334, slots 336 and stems 338. The slots 336 are shown as being positioned circumferentially about distal coupling section 332 in 90° intervals such that distal coupling section 332 comprises four slots. The slots 336 permit the head 334 to compress radially inward as the distal coupling section 332 is pressed into the proximal receiving portion 322 and begins to enter head receiving portion 324. Of course, any number of slots could be utilized (1, 2, 3, etc.), depending on a variety of factors (material selection, connection configuration, etc.) in order to maximize the effectiveness of the connection.

Catheter connector system 300 is assembled similarly to that described above with catheter connector system 100. Catheter 110 is placed within the patient and, if necessary, may be proximally trimmed to a suitable length. With a portion of the catheter 110 extending from the proximal end of the boot 320, the stems 338 of the bifurcation assembly 330 are pressed into lumens 112, 114 of catheter 110, after which the distal coupling section 332 is pressed into the proximal receiving portion 322. When the head 334 has been fully received by head receiving portion 324 (i.e., has been pressed beyond shoulder 326 of head receiving portion 324), the geometry thereof permits head 334 to expand outward, at which point there is an audible "click," effectively locking bifurcation assembly 330 to boot 320. Once assembled, the portions of the distal coupling section 332 surrounding the stems 338 act to seal the catheter 110 against the stems 338 for a fluid-tight connection. As with catheter connector system 100, the locking connection of catheter connector system 300 may be permanent or releasable.

Figure 11:
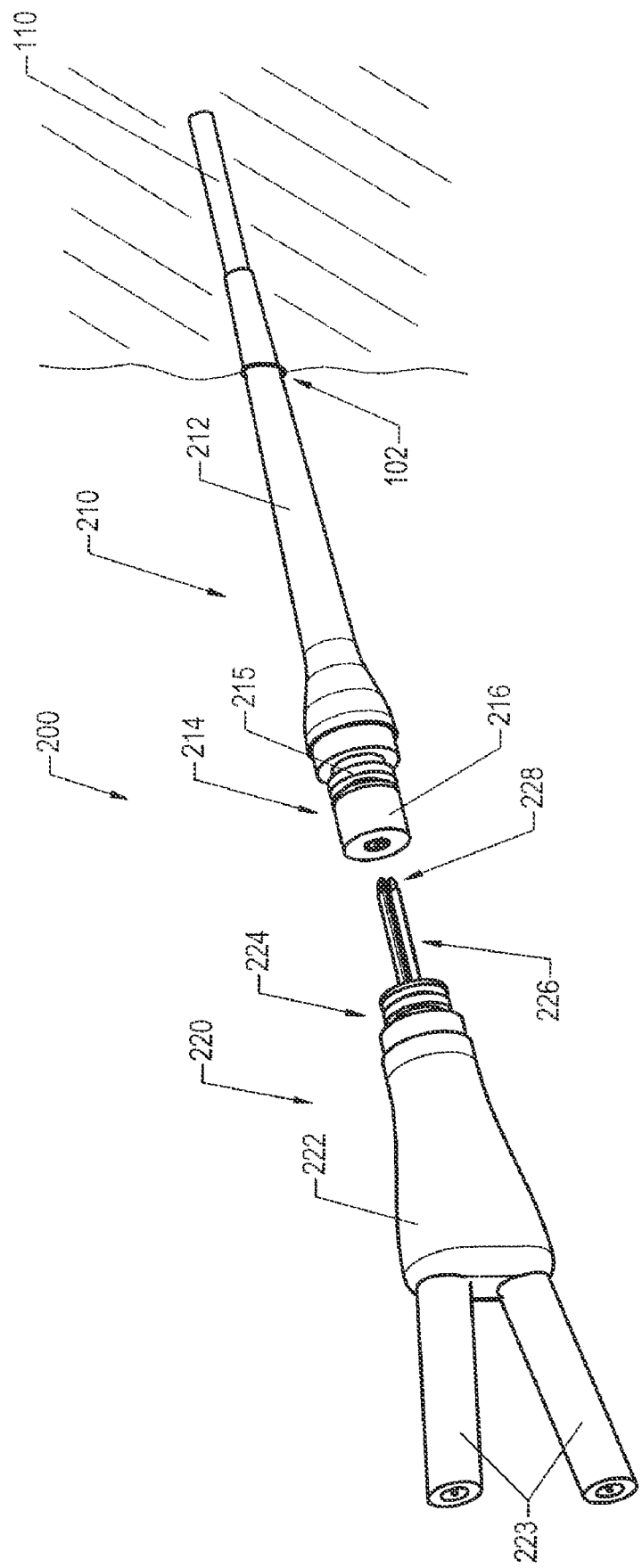
FIG. 11 is a perspective view of an alternate embodiment of a catheter connector system according to the present invention.
Figure 12:
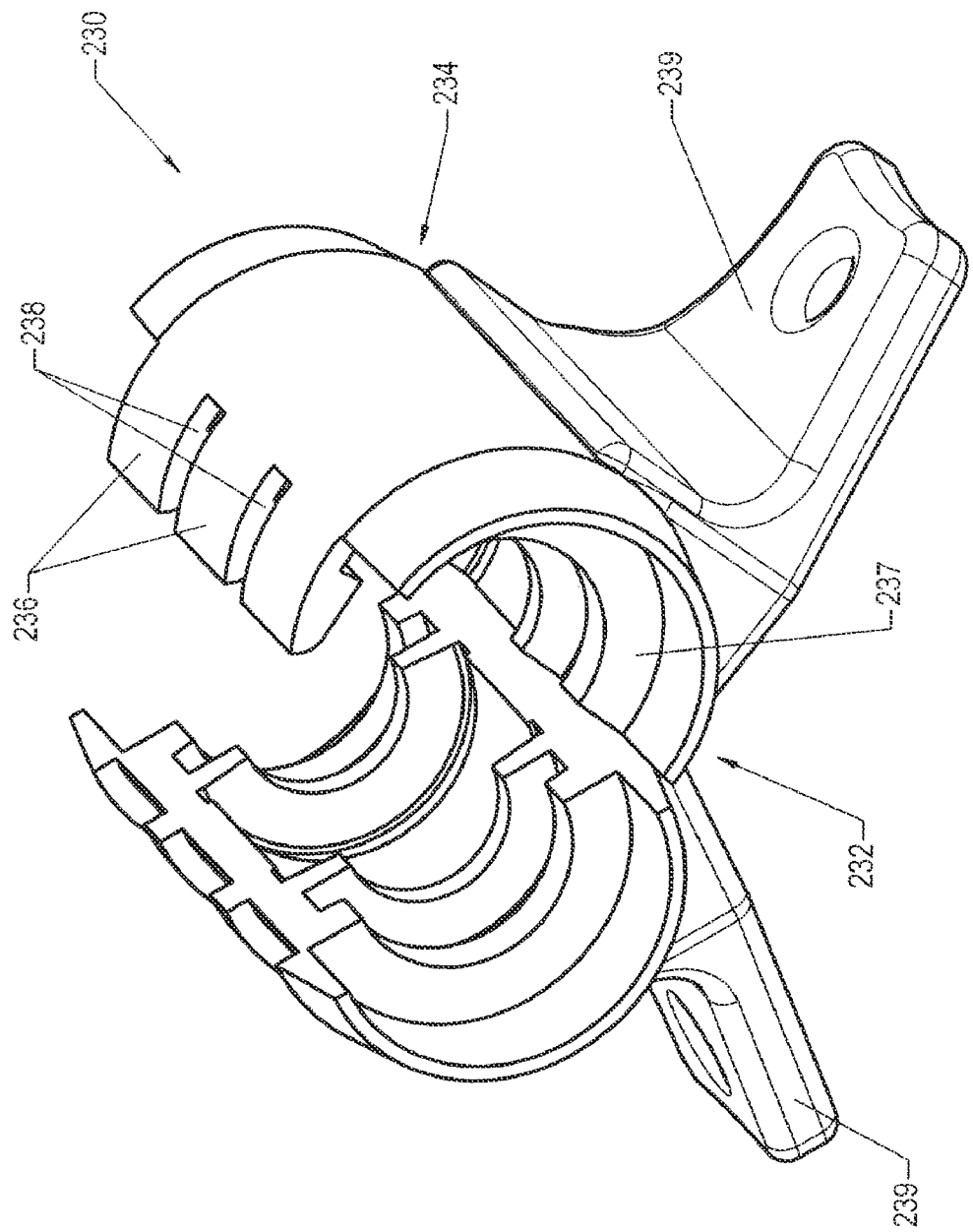
FIG. 12 is an enlarged view of a clamp according to the present invention.

In another embodiment of the present invention, a catheter connector system 200 is illustrated in FIGS. 11-12, having a boot 210, a bifurcation assembly 220 and a clamp 230. The catheter connector system 200 is shown prior to attachment of the bifurcation assembly 220, with the boot 210 slid over a catheter 202 and into the venipuncture site 102, the catheter 110 having been trimmed at its proximal end to lie flush with the proximal end of the boot 210. The boot 210 has incorporated in its proximal end a connector member 214, which has a distal portion 215 with grooves to optimize locking connection with the clamp 230, and a proximal portion 216 having an energized seal design, which in the preferred embodiment is made of a soft material (e.g., silicone with a durometer of 30). The boot 210 has a distal taper, which allows it to be slid into the venipuncture site to not only seal the site from extraneous bleeding, but also to protect the extracorporeal portion of the catheter from breakage.

The bifurcation assembly 220 has a connector member 224 at the distal end thereof, having a similar configuration to that of the distal portion 215 of the connector member 214. Extending from the connector member 224 are a pair of stems 226, which can be made of metal or other hard or hardened material, for insertion into the lumens of catheter 110, similar to that described above in connection with catheter connector system 100. Also included in the bifurcation assembly 220 is a hub 222 and extension tubes 223. In one embodiment, the boot body 212 and the bifurcation assembly body 222, as well as the extension legs 223 are made of a soft elastomer material (e.g., medical grade polyurethanes and silicones). Certainly, however, many materials are possible and would equally be within the scope of the invention. In one embodiment, the bifurcation assembly 220 is shipped pre-assembled to the boot 210.

The clamp 230 is in a clamshell configuration having locking opposed halves 234 that are connected by a bottom hinge 232. The interlocking halves 234 comprise teeth 236, separated by gaps 238, the teeth 236 on one half corresponding positionally with the gaps 238 on the opposite half when the clamp 230 is in a closed condition. The teeth 236 and gaps 238 are configured to create an interference fit (i.e., mechanical lock) when in a closed position to prevent inadvertent opening under normal pressures. The interlocking halves 234 also include ring portions 237 on the inside thereof, which create axial compression upon closing around the connector members 214, 224 and also ensure the tensile integrity of the assembly. It should be appreciated that, although the clamp 230 is shown in a particular configuration with respect to teeth 236, ring portions 237 and gaps 238, many other configurations would be equally within the scope of the present invention, the primary considerations being that the clamp 230 be shaped to lock around the connector members 214, 224 of the boot 210 and bifurcation assembly 220 so that inadvertent opening is prevented and to provide a seal against the catheter within the boot connector member 214 as will be described in more detail below. Also incorporated into the clamp 230 are suture wings 239 having openings adapted for attachment to a patient (through either direct means or indirect means as discussed above). The suture wings 239 can be integrally formed with the clamp 230 (e.g., via injection molding) or alternatively may be molded over the interlocking halves 234. In one embodiment, the interlocking halves 234 are made of a semi-rigid plastic, while the suture wings 239 are made of a soft elastomer material.

As stated, assembly of the catheter connector system 200 is initiated by placing the catheter 110 within the body of a patient using traditional methods, such that a length of catheter 110 extends from the venipuncture site 102. Upon confirmation of correct catheter placement, the clinician holds the proximal end of the catheter 110 and slides the boot 210 over the catheter 110 and into the venipuncture site 102. A dilator may be used to position the boot 210 over the catheter as described above, or other means of positioning the boot 210 over the catheter 110 may be utilized as would be known to one of skill in the art. In one embodiment, an expander is inserted/activated under the distal end of the boot 210 after it has been positioned in the venipuncture site in order to create a seal between the catheter 110 and the boot 210 to prevent blood fluids from wicking between the components and to create a friction fit between the components, which could facilitate assembly thereof. Following positioning of the boot 210 over the catheter 110, the proximal end of the catheter 110 extending from the connector member 214 of the boot 210 is trimmed, the clinician utilizing the surface of the proximal portion 216 of the connector member 214 as a guide, resulting in a flush outer surface thereof.

While firmly holding the boot 210, the bifurcation assembly 220 is then connected to the boot 210 by inserting stems 226 into the lumens of the catheter 110 until the connector members 214, 224 meet. As with catheter connector system 100, in the case of a single lumen catheter, only one stem would be provided; moreover, the cross-sectional shape of the stem may correspond to the cross-sectional shape of the lumen to provide a fluid tight connection. Round-nosed obturators 228 may be employed to facilitate the insertion of the stems 226 into the lumens of the catheter 110 and to prevent material damage during the insertion process, which can occur in small catheters (e.g., 5 Fr or 6 Fr). The obturators 228 are inserted through the extension legs 223 and the lumens within the body 222 of the bifurcation assembly 220 to emerge through the stems 226 (FIGS. 11 and 14). The obturators 228 can be removed after assembly, for example, by using stylets that are insert molded into the obturators 228 and extend past the luer connectors at the proximal end of each extension leg 223.

Finally, the clamp 230 is oriented so that the suture wings 239 are parallel to the top and bottom surfaces of the boot 210 and the bifurcation assembly 220 (i.e., the bottom surface being that surface adjacent the skin of the patient) and is closed around the connector members 214, 224. As the clamp 230 closes, the mating surfaces on the connector members 214, 224 and the interlocking halves 234 interact to compress the proximal portion 216 of the connector member 214. The incompressible nature of the material thereof causes the outer diameter of the proximal portion 216 to increase and its inner diameter to decrease. The inside surface of the clamp 230 minimizes the change in the outside diameter and maximizes the decrease in the inside diameter, which equates to a compressive force on the catheter 110, resulting in a seal against the stems 226 inserted into the lumens thereof. Following locking of the clamp, the obturators are removed and the suture wings 239 are utilized to affix the system 200 to the skin of the patient.

Figure 13:
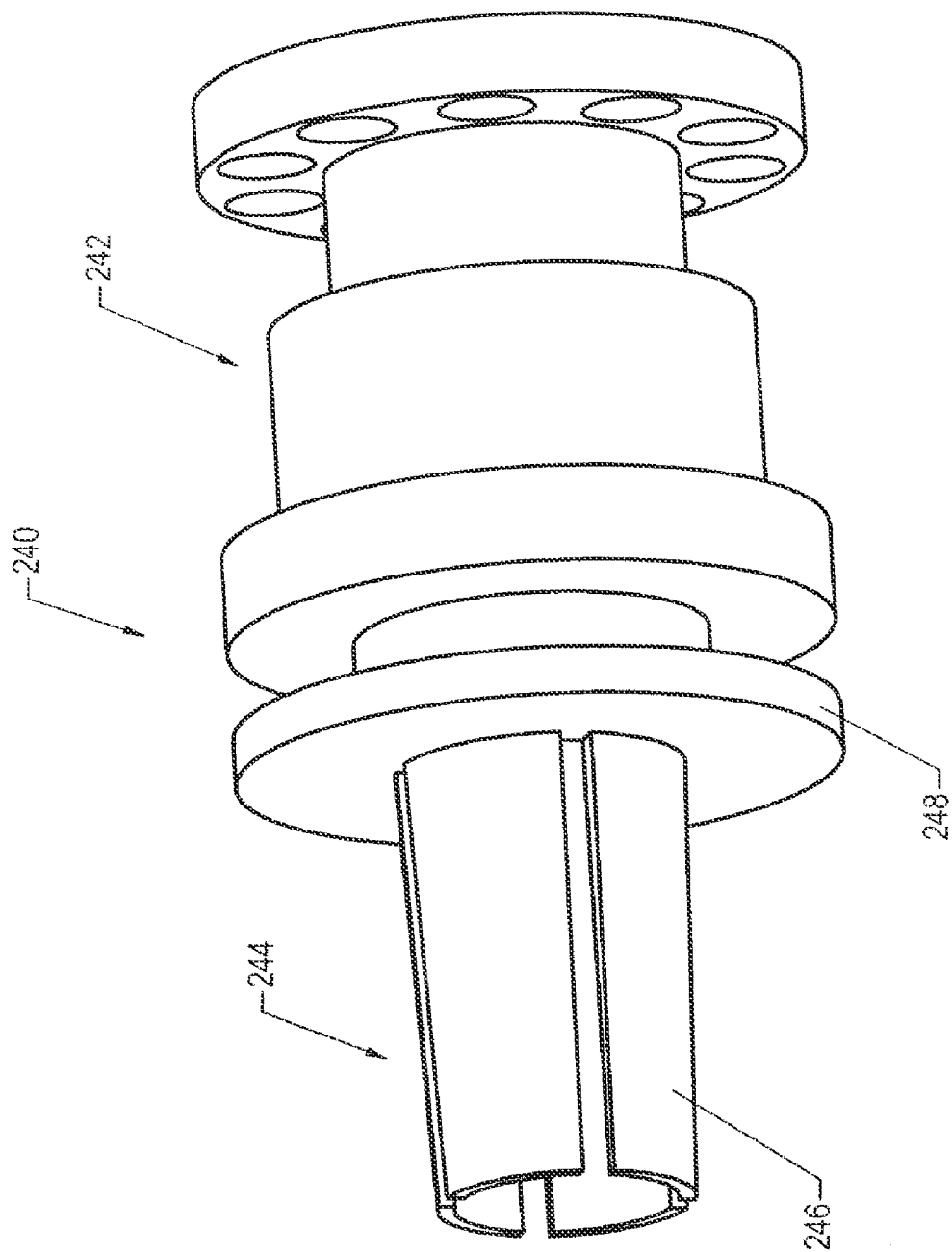
FIG. 13 is a perspective view of a collet type connector member according to the present invention.

In one variation of the catheter connector system 200, a slightly different connector member 240 is utilized, having a collet design as shown in FIG. 13. The connector member 240 may be made of a semi-rigid plastic and has a distal portion 242 that is attached to the boot 210 and an insert portion 244 extending from the proximal end of the boot 210. The bifurcation assembly connector member 224 has a receiving bore to permit entry and locking of the insert portion 244 therein. The insert portion 244 has a frustoconical shape with individual sectioned panels 246 attached to a base 248. The sectioned panels 246 flex inward as they are received within the bore of the connector member 224, reducing the inside diameter of the insert portion 244 and thereby creating a compressive seal on the catheter. As the insert portion 244 is received within the bore of the connector member 224, a snap fit (i.e., a mechanical lock) occurs due to the configuration of the bore as can be seen in FIG. 14. All other aspects of assembly of the bifurcation assembly 220 to the boot 210 are as described above. An exploded cross-sectional view of the catheter connector system 200 employing the collet design is shown in FIG. 15.

It should be noted that more attention to detail is required in trimming the proximal end of the catheter when utilizing the collet design, as opposed to the energized seal design, as the insert portion 244 will often be made of a harder material. As a result, haphazard trimming can produce burrs on the face of the insert portion 244, which could lead to problems. It should further be noted that unlike the energized seal design, the clamp 230 does not impact the sealing operation and instead only serves to keep the bifurcation assembly 220 and boot 210 connected. The seal is created upon insertion of the insert portion 244 into the bore of the connector member 224. It should be appreciated that when the clamp is closed around the connector members 224, 240 in the collet design, an external closure is provided to the mechanical lock created by the insertion of the insert portion 244 into the bore of the connector member 224, the expected result of which is that the assembled system 200 will have a significantly higher tensile capability than the individual components.

The present invention has been described above in terms of certain preferred embodiments so that an understanding of the present invention can be conveyed. However, there are many alternative arrangements for a catheter connector not specifically described herein, but with which the present invention is applicable. Although specific features have been provided, the catheter connector of the present invention would equally be embodied by other configurations not specifically recited herein. The scope of the present invention should therefore not be limited by the embodiments illustrated, but rather it should be understood that the present invention has wide applicability with respect to catheter systems generally. All modifications, variations, or equivalent elements and implementations that are within the scope of the appended claims should therefore be considered within the scope of the invention.

What is claimed is:

1. A kit for connecting a catheter to extracorporeal medical equipment, comprising:
    a boot comprising a tapered outer wall having a diameter that decreases toward a distal end thereof, said outer wall enclosing a longitudinally extending lumen, wherein said boot lumen is sized to prevent axial movement of said catheter when said catheter is positioned therein;
    a bifurcation assembly, comprising at least one extension leg extending from a proximal end thereof and at least one stem extending from a distal end thereof, wherein said at least one stem is configured to be received into a lumen of said catheter; and
    a dilator comprising a shaft having an outer wall enclosing a longitudinally extending lumen, said shaft configured to expand said boot lumen when positioned therein, said dilator lumen configured for slideable movement over said catheter.

2. The kit according to claim 1, further comprising at least one obturator, having a rounded tip, positioned through said extension leg and said stem.

3. The kit according to claim 1, wherein said boot further comprises a pair of suture wings laterally extending from said outer wall.

4. The kit according to claim 1, wherein said catheter has an outer wall with a diameter smaller than the diameter of said dilator lumen.

5. The kit according to claim 4, wherein said dilator lumen diameter is at least approximately 0.025 mm greater than said catheter outer wall diameter.

6. The kit according to claim 1, wherein said dilator further comprises a transition section positioned at a distal end of said shaft, wherein said transition region is tapered such that the diameter thereof decreases toward a distal end thereof.

7. The kit according to claim 6, wherein said transition section further comprises a rounded tip.

8. The kit according to claim 1, wherein at least a portion of said dilator shaft outer wall contains a lubricant thereon.

9. The kit according to claim 1, wherein said dilator further comprises a handle positioned proximal said shaft.

10. The kit according to claim 9, wherein said handle comprises a fin and a base.

11. The kit according to claim 10, wherein at least one of said fin and base comprises a finger grip.

12. A kit for connecting a catheter to extracorporeal medical equipment, comprising:
    a boot comprising a tapered outer wall, having a diameter that decreases toward a distal end thereof and enclosing a longitudinally extending lumen, and a first connector member positioned at a proximal end thereof;
    a bifurcation assembly, comprising at least one extension leg extending from a proximal end thereof and a second connector member positioned at a distal end thereof, said second connector member having at least one stem extending therefrom, said stem being configured to be received into a lumen of said catheter;
    a clamp configured to lock around said first and second connector members; and
    at least one obturator, having a rounded tip, positioned through said extension leg and said stem.

13. The kit according to claim 12, further comprising a dilator comprising a shaft having an outer wall enclosing a longitudinally extending lumen, said shaft configured to expand said boot lumen when positioned therein, said dilator lumen configured for slideable movement over said catheter.

14. The kit according to claim 12, wherein said bifurcation assembly comprises a first and second extension leg in fluid communication with a first and second stem.

15. The kit according to claim 14, comprising a first and second obturator positioned respectively through said first and second extension legs and said first and second stems.

16. A proximally trimmable catheter system, comprising:
    a catheter comprising at least one lumen;
    a boot comprising a tapered outer wall having a diameter that decreases toward a distal end thereof, said outer wall enclosing a longitudinally extending lumen, wherein said boot lumen is sized to prevent axial movement of said catheter when said catheter is positioned therein;
    a bifurcation assembly, comprising at least one extension leg extending from a proximal end thereof and at least one stem extending from a distal end thereof, wherein said at least one stem is configured to be received into a lumen of said catheter; and
    a dilator comprising a shaft having an outer wall enclosing a longitudinally extending lumen, said shaft configured to expand said boot lumen when positioned therein, said dilator lumen configured for slideable movement over said catheter.

17. The system according to claim 16, further comprising at least one obturator, having a rounded tip, positioned through said extension leg and said stem.

18. The system according to claim 16, wherein said boot further comprises a pair of suture wings laterally extending from said outer wall.

19. The system according to claim 16, wherein said catheter comprises a first and second lumen, each having a generally trapezoidal cross-sectional shape.

20. The system according to claim 19, wherein said bifurcation assembly comprises a first and second extension leg in fluid communication with a first and second stem, said first and second stems each having a generally trapezoidal cross-sectional shape.

* * * * *